US009339275B2

(12) United States Patent
Trommeter et al.

(10) Patent No.: US 9,339,275 B2
(45) Date of Patent: May 17, 2016

(54) SYSTEMS, DEVICES, AND METHODS FOR DELIVERING A LUMEN OCCLUSION DEVICE USING DISTAL AND/OR PROXIMAL CONTROL

(71) Applicant: EndoShape, Inc., Boulder, CO (US)

(72) Inventors: Julie Trommeter, Boulder, CO (US); Charles Barkenbus, Boulder, CO (US); Jeffrey Castleberry, Boulder, CO (US); William Aldrich, Boulder, CO (US); Jon Page, Boulder, CO (US); Paul Burek, Boulder, CO (US); Stan Needle, Boulder, CO (US); Frank Becking, Palo Alto, CA (US); Dean Carson, Boulder, CO (US); Jessi Watson, Boulder, CO (US)

(73) Assignee: ENDOSHAPE, INC., Boulder, CO (US)

( * ) Notice: Subject to any disclaimer, the term of this patent is extended or adjusted under 35 U.S.C. 154(b) by 322 days.

(21) Appl. No.: 13/750,854

(22) Filed: Jan. 25, 2013

(65) Prior Publication Data

US 2014/0039542 A1    Feb. 6, 2014

Related U.S. Application Data

(60) Provisional application No. 61/591,119, filed on Jan. 26, 2012, provisional application No. 61/681,507, filed on Aug. 9, 2012.

(51) Int. Cl.
*A61M 29/00* (2006.01)
*A61B 17/12* (2006.01)
(Continued)

(52) U.S. Cl.
CPC ....... *A61B 17/12145* (2013.01); *A61B 17/1214* (2013.01); *A61B 17/12022* (2013.01);
(Continued)

(58) Field of Classification Search
CPC .................. A61B 17/1214; A61B 17/12022; A61B 17/12031; A61B 2017/12054; A61B 2017/1205; A61B 17/1245; A61B 17/12109; A61B 2/022; A61F 2002/011
USPC ......................................................... 606/200
See application file for complete search history.

(56) References Cited

U.S. PATENT DOCUMENTS 5,250,071 A * 10/1993 Palermo ........................ 606/198
5,304,195 A     4/1994 Twyford, Jr. et al.
(Continued)

FOREIGN PATENT DOCUMENTS

CN          101310681 A    11/2008

OTHER PUBLICATIONS

Boston Scientific Interlock™ Brochure, 2006.
(Continued)

*Primary Examiner* — Sarah W Aleman
*Assistant Examiner* — Chima Igboko
(74) *Attorney, Agent, or Firm* — One LLP

(57) ABSTRACT

A delivery apparatus for a lumen occlusion device includes a pusher configured for releasably coupling with and pushing and pulling a proximal end of the occlusion device in a distal or proximal direction and a distal control wire capable of releasably coupling with the distal end and the proximal end of the occlusion device. The control wire may be configured for moving the distal end of the occlusion device in both proximal and distal directions allowing precise simultaneous control of both proximal and distal ends of the occlusion device. Control of both ends provides for placing the occlusion device in tension during delivery through a delivery catheter, thereby reducing delivery forces, achieving greater compaction of the occlusion device in the lumen, and precisely locating both distal and proximal ends of the occlusion device within the lumen.

21 Claims, 18 Drawing Sheets

(51) Int. Cl.
*A61F 2/01* (2006.01)
*A61B 19/00* (2006.01)

(52) U.S. Cl.
CPC ..... *A61B17/12031* (2013.01); *A61B 17/12109* (2013.01); *A61B 17/12113* (2013.01); *A61B 2017/12054* (2013.01); *A61B 2019/5466* (2013.01); *A61F 2/01* (2013.01)

(56) References Cited

U.S. PATENT DOCUMENTS

| | | | |
|---|---|---|---|
| 5,578,045 A | 11/1996 | Das | |
| 5,601,600 A | 2/1997 | Ton | |
| 5,800,455 A * | 9/1998 | Palermo et al. | 606/191 |
| 5,853,422 A * | 12/1998 | Huebsch et al. | 606/213 |
| 5,916,235 A | 6/1999 | Guglielmi | |
| 6,027,519 A * | 2/2000 | Stanford | 606/198 |
| RE37,117 E | 3/2001 | Palermo | |
| 6,375,668 B1 | 4/2002 | Gifford et al. | |
| 7,691,124 B2 | 4/2010 | Balgobin | |
| 8,034,094 B2 * | 10/2011 | Aoba et al. | 623/1.11 |
| 2001/0002438 A1 | 5/2001 | Sepetka et al. | |
| 2004/0034363 A1 * | 2/2004 | Wilson et al. | 606/108 |
| 2004/0193178 A1 | 9/2004 | Nikolchev | |
| 2004/0220610 A1 | 11/2004 | Kreidler et al. | |
| 2005/0038470 A1 * | 2/2005 | van der Burg et al. | 606/213 |
| 2005/0177182 A1 * | 8/2005 | van der Burg et al. | 606/157 |
| 2005/0192620 A1 | 9/2005 | Cully et al. | |
| 2005/0228438 A1 * | 10/2005 | Sachar et al. | 606/200 |
| 2005/0273135 A1 * | 12/2005 | Chanduszko et al. | 606/213 |
| 2005/0288786 A1 * | 12/2005 | Chanduszko | 623/11.11 |
| 2006/0116714 A1 * | 6/2006 | Sepetka et al. | 606/200 |
| 2006/0122647 A1 * | 6/2006 | Callaghan et al. | 606/213 |
| 2006/0136037 A1 | 6/2006 | DeBeer et al. | |
| 2006/0155323 A1 * | 7/2006 | Porter et al. | 606/200 |
| 2006/0271097 A1 * | 11/2006 | Ramzipoor et al. | 606/200 |
| 2006/0276827 A1 | 12/2006 | Mitelberg et al. | |
| 2007/0010849 A1 | 1/2007 | Balgobin et al. | |
| 2007/0010850 A1 * | 1/2007 | Balgobin et al. | 606/200 |
| 2007/0055302 A1 * | 3/2007 | Henry et al. | 606/200 |
| 2007/0083226 A1 * | 4/2007 | Buiser et al. | 606/200 |
| 2007/0167981 A1 * | 7/2007 | Opolski et al. | 606/213 |
| 2007/0221230 A1 | 9/2007 | Thompson et al. | |
| 2007/0276415 A1 * | 11/2007 | Kladakis et al. | 606/151 |
| 2008/0039922 A1 | 2/2008 | Miles et al. | |
| 2008/0119887 A1 * | 5/2008 | Que et al. | 606/200 |
| 2008/0300616 A1 * | 12/2008 | Que et al. | 606/191 |
| 2008/0306503 A1 | 12/2008 | Que et al. | |
| 2009/0036877 A1 | 2/2009 | Nardone et al. | |
| 2009/0138023 A1 * | 5/2009 | Johnson et al. | 606/108 |
| 2009/0270974 A1 * | 10/2009 | Berez et al. | 623/1.17 |
| 2009/0287291 A1 | 11/2009 | Becking et al. | |
| 2009/0312748 A1 * | 12/2009 | Johnson et al. | 606/1 |
| 2010/0070050 A1 * | 3/2010 | Mathis et al. | 623/23.65 |
| 2010/0160944 A1 | 6/2010 | Teoh et al. | |
| 2010/0168834 A1 | 7/2010 | Ryan et al. | |
| 2010/0174269 A1 * | 7/2010 | Tompkins et al. | 604/507 |
| 2010/0185233 A1 * | 7/2010 | Thommen | 606/213 |
| 2010/0262177 A1 | 10/2010 | Frigstad et al. | |
| 2010/0324586 A1 | 12/2010 | Miles et al. | |
| 2011/0092997 A1 | 4/2011 | Kang | |
| 2011/0184456 A1 * | 7/2011 | Grandfield et al. | 606/200 |
| 2012/0172927 A1 * | 7/2012 | Campbell et al. | 606/213 |

OTHER PUBLICATIONS

ISR PCT/US2013/023306, dated Mar. 22, 2013.
CN, 201380016522.4 First Office Action, Jul. 31, 2015.

* cited by examiner

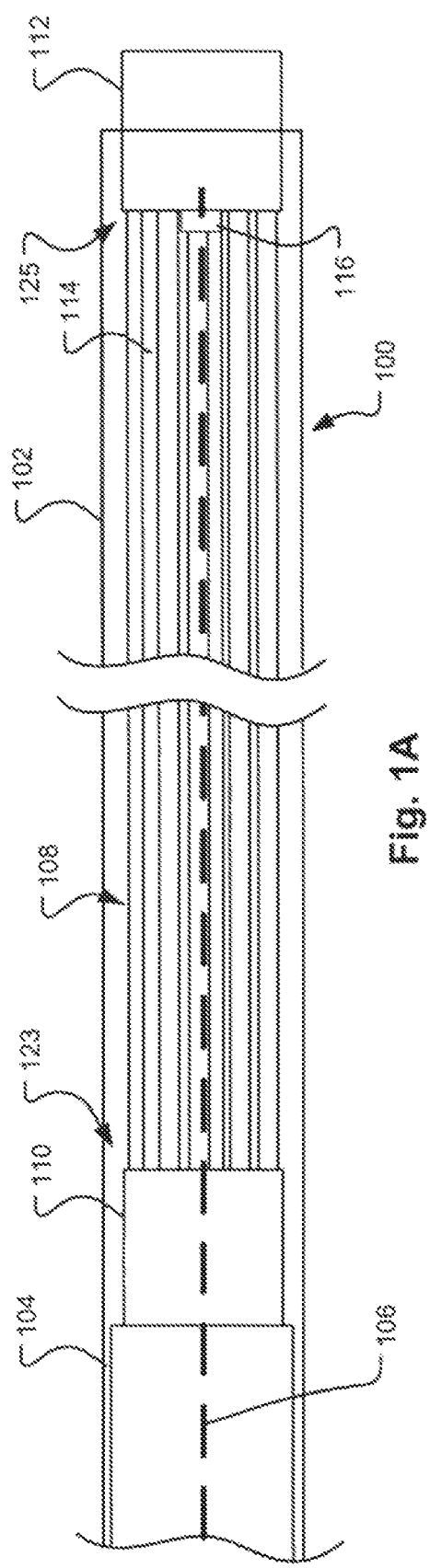
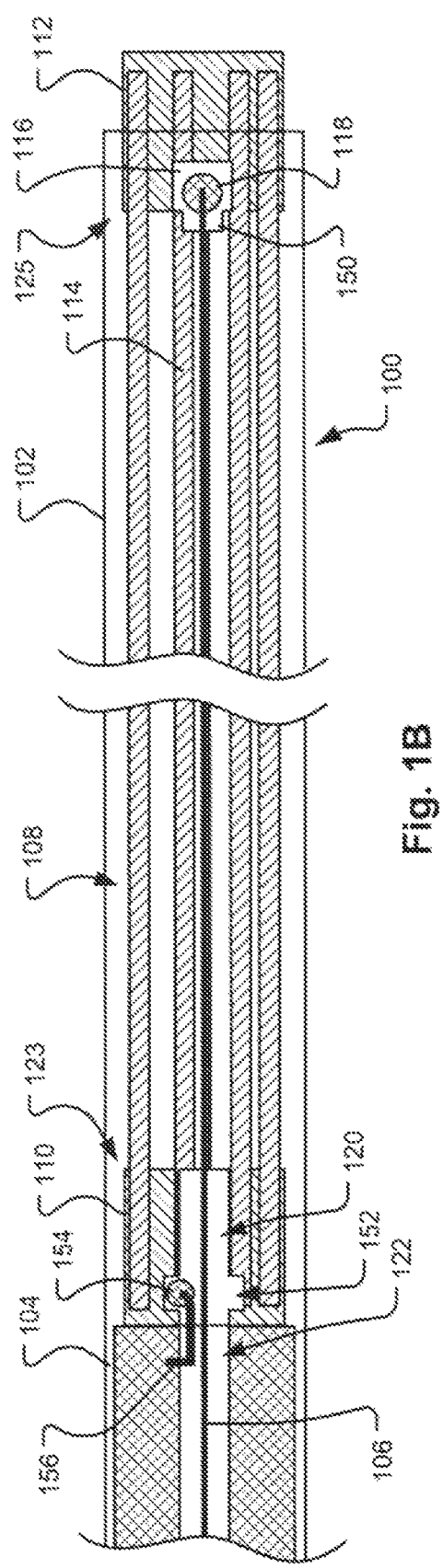

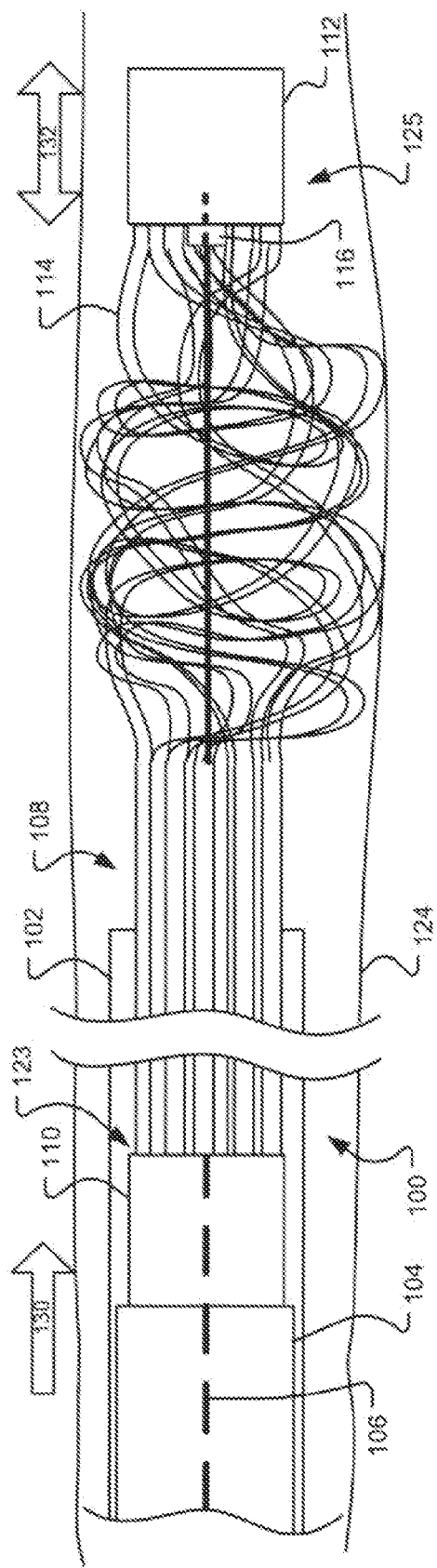
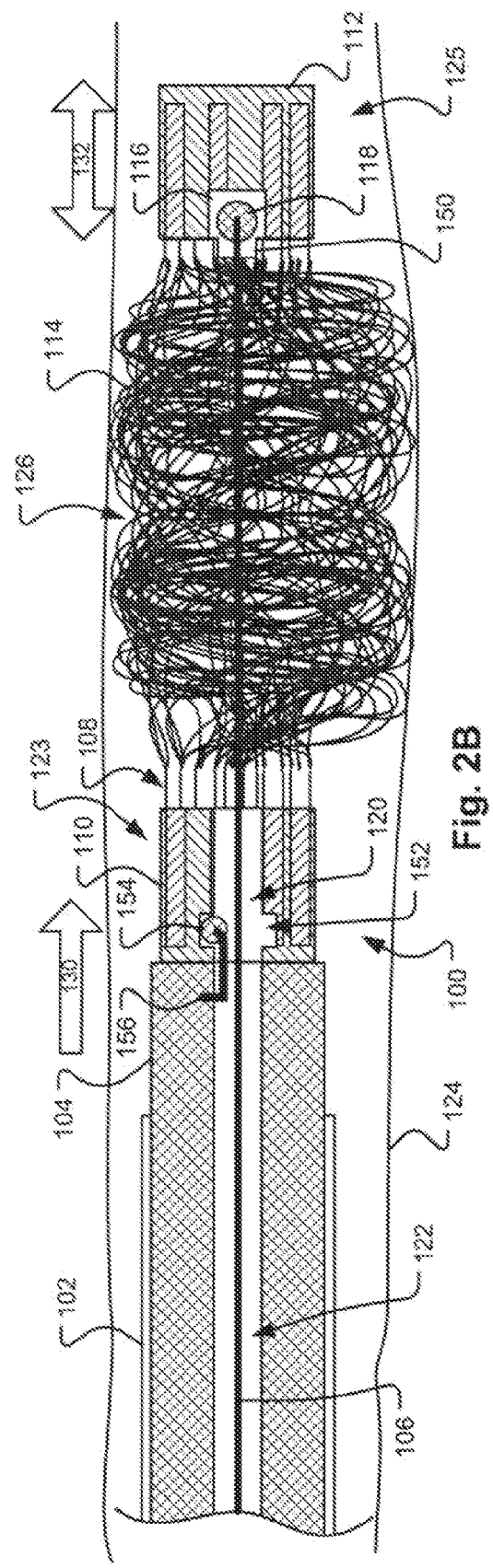
Fig. 2A
Fig. 2B

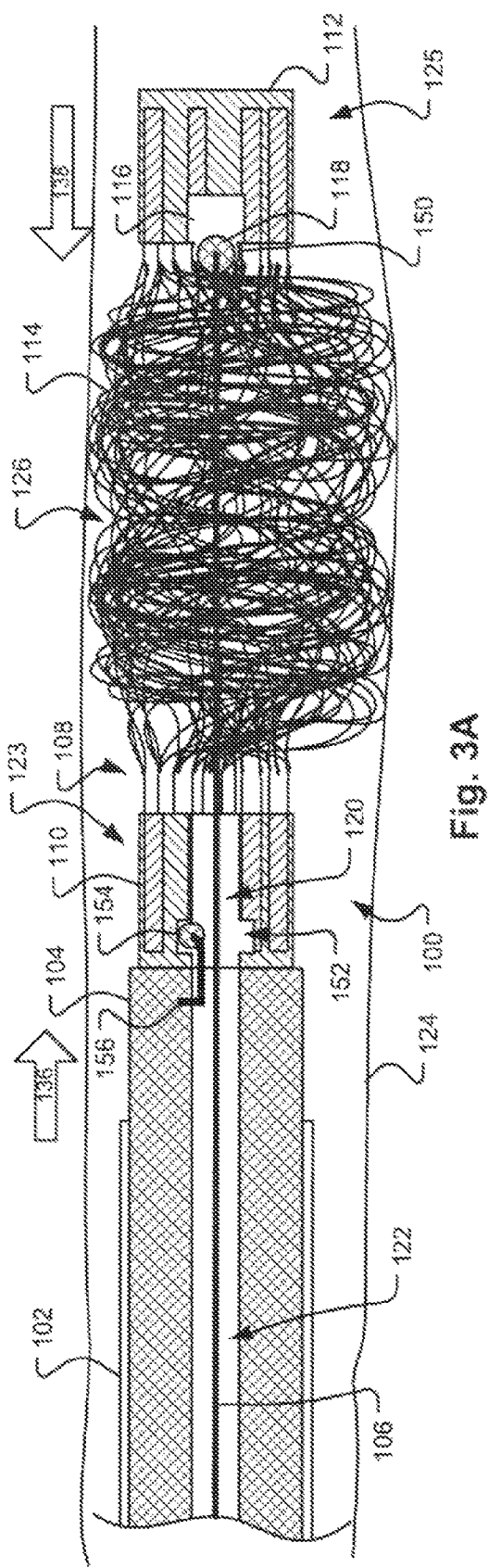
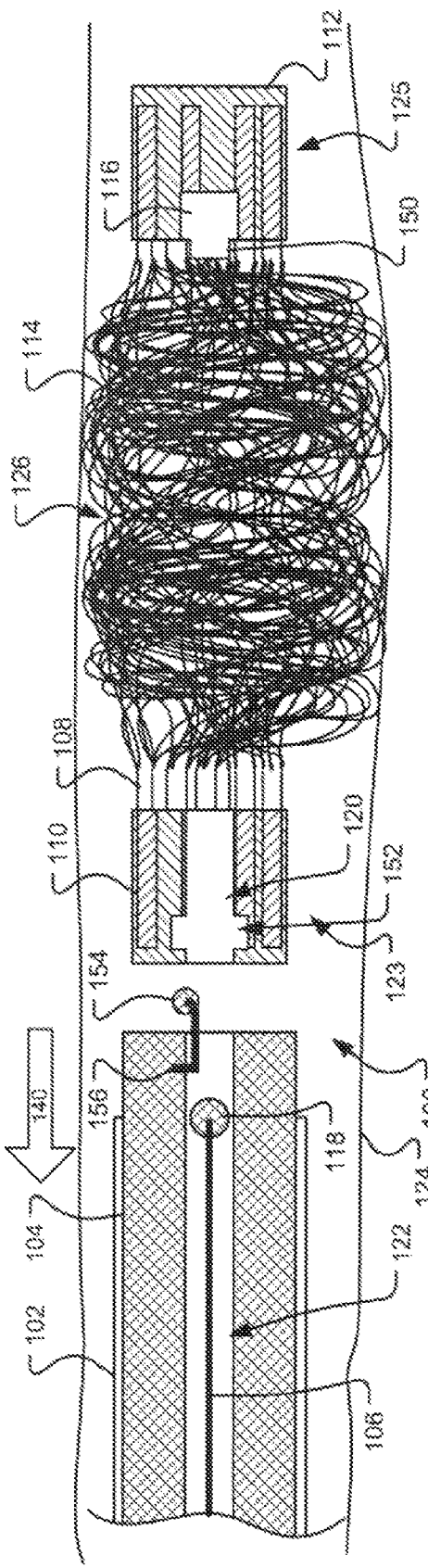
Fig. 3A
Fig. 3B

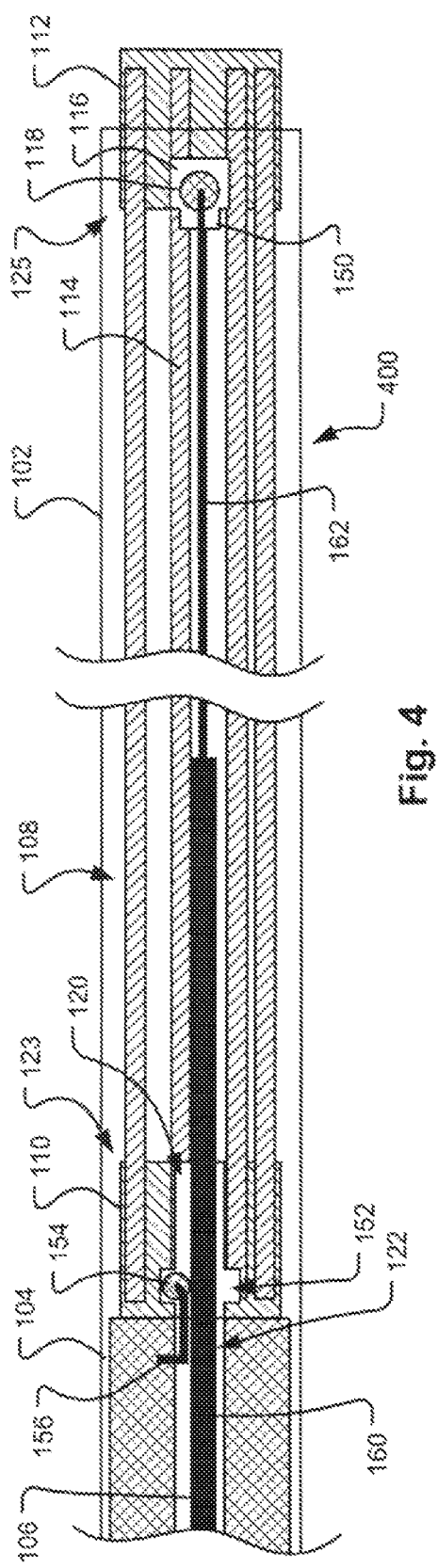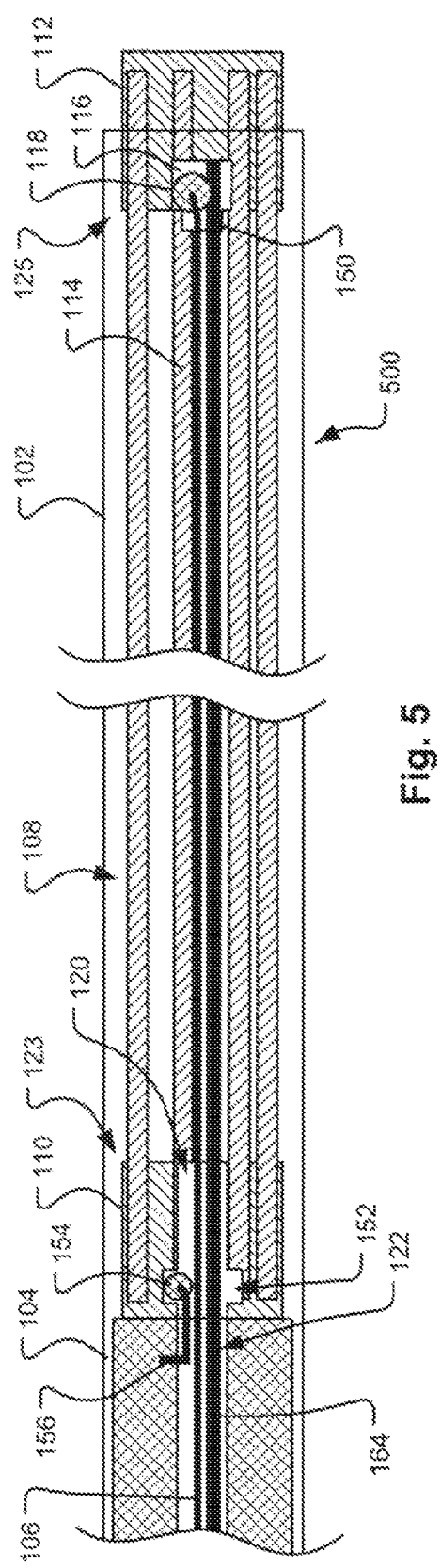

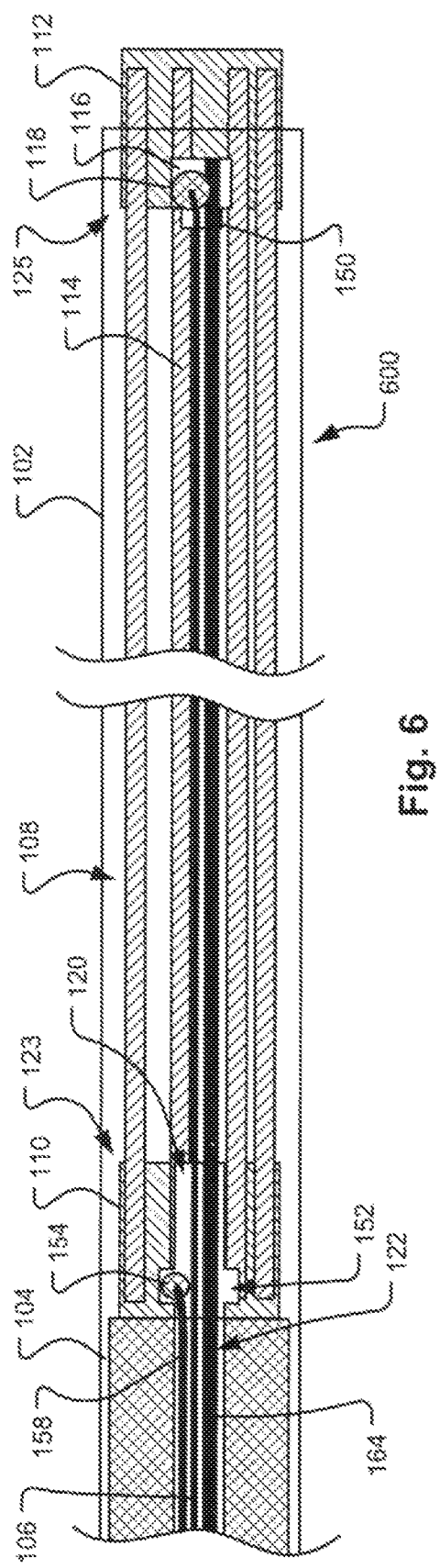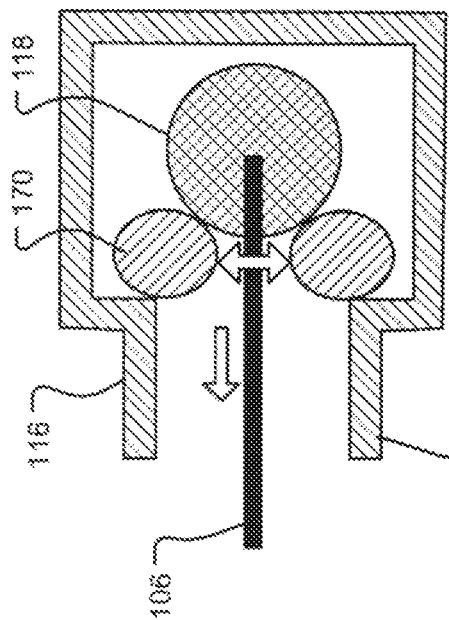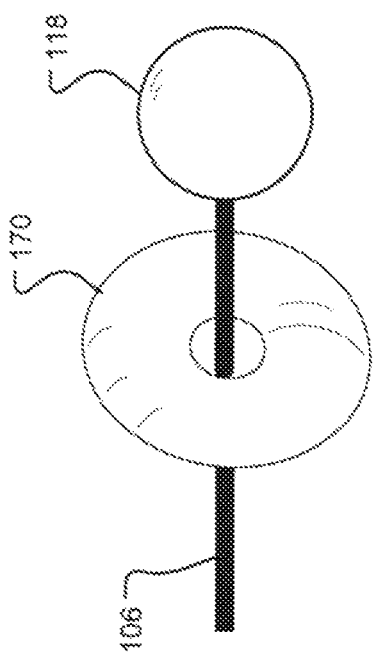

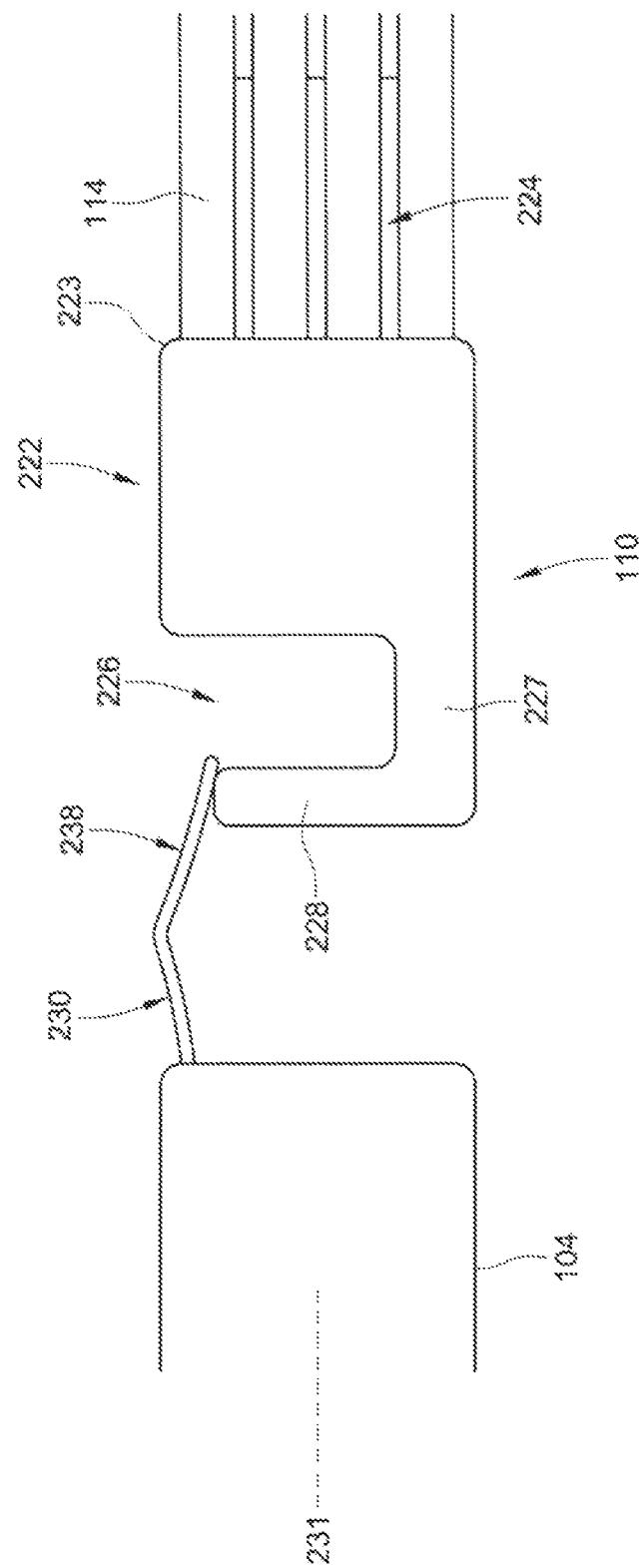

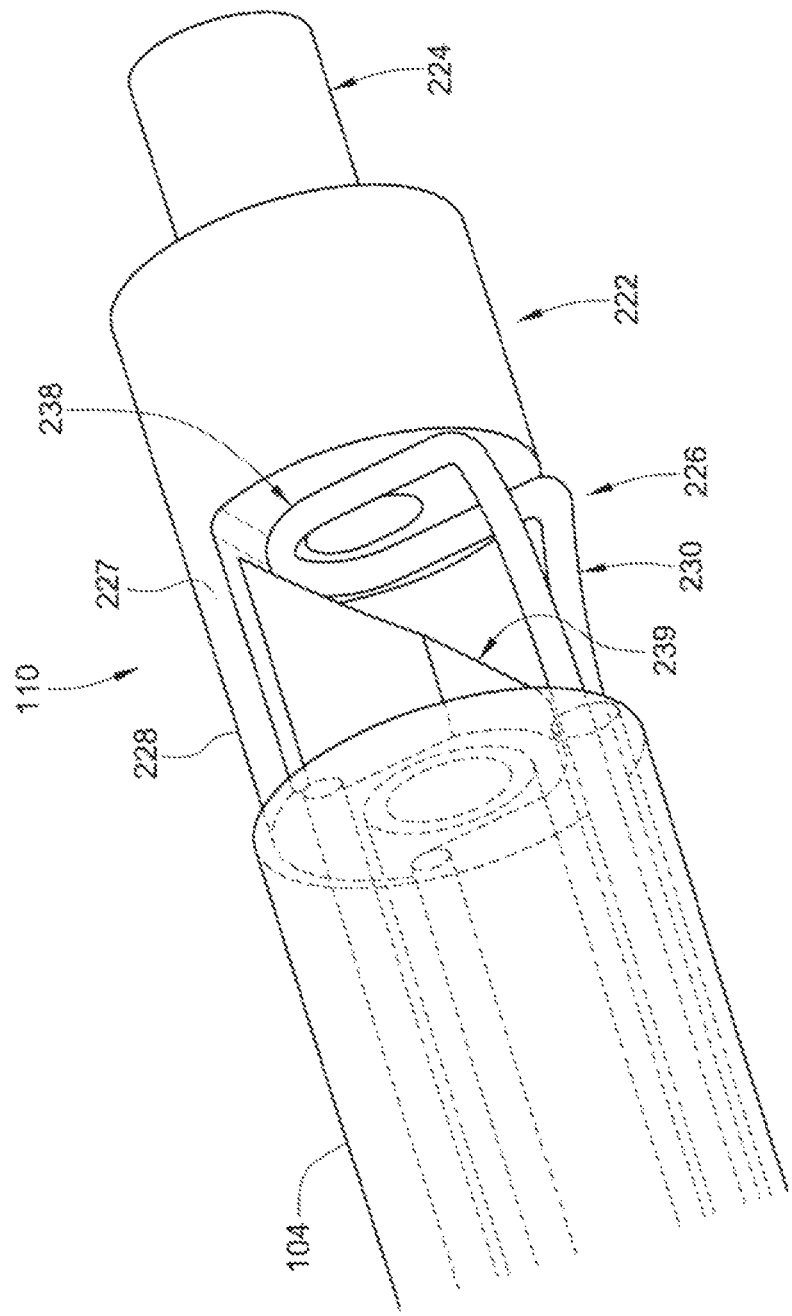

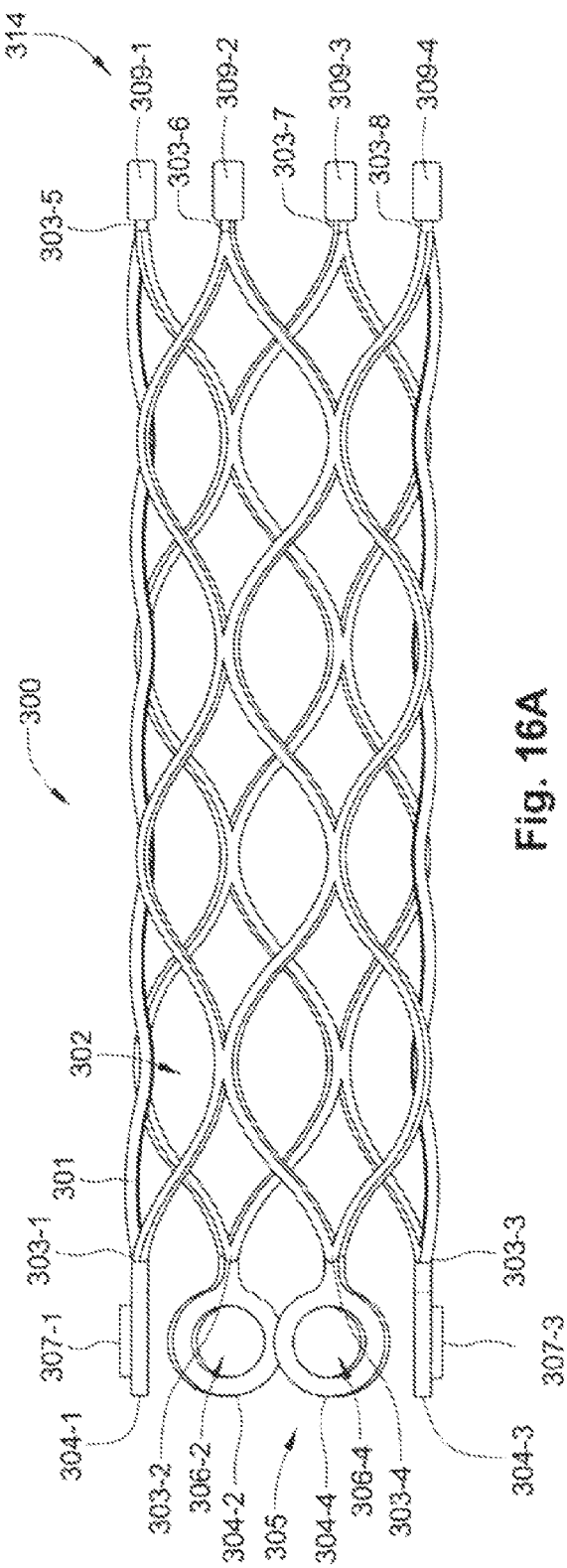
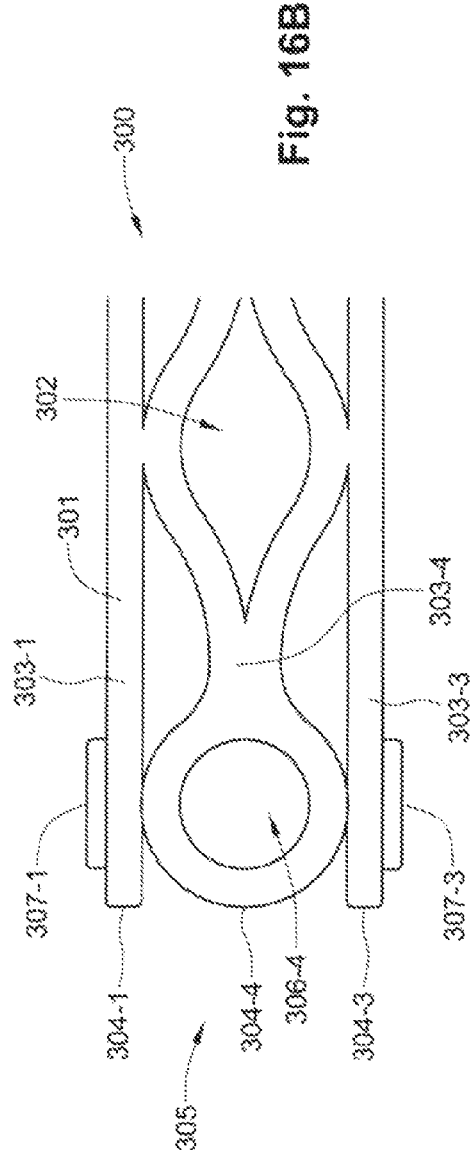

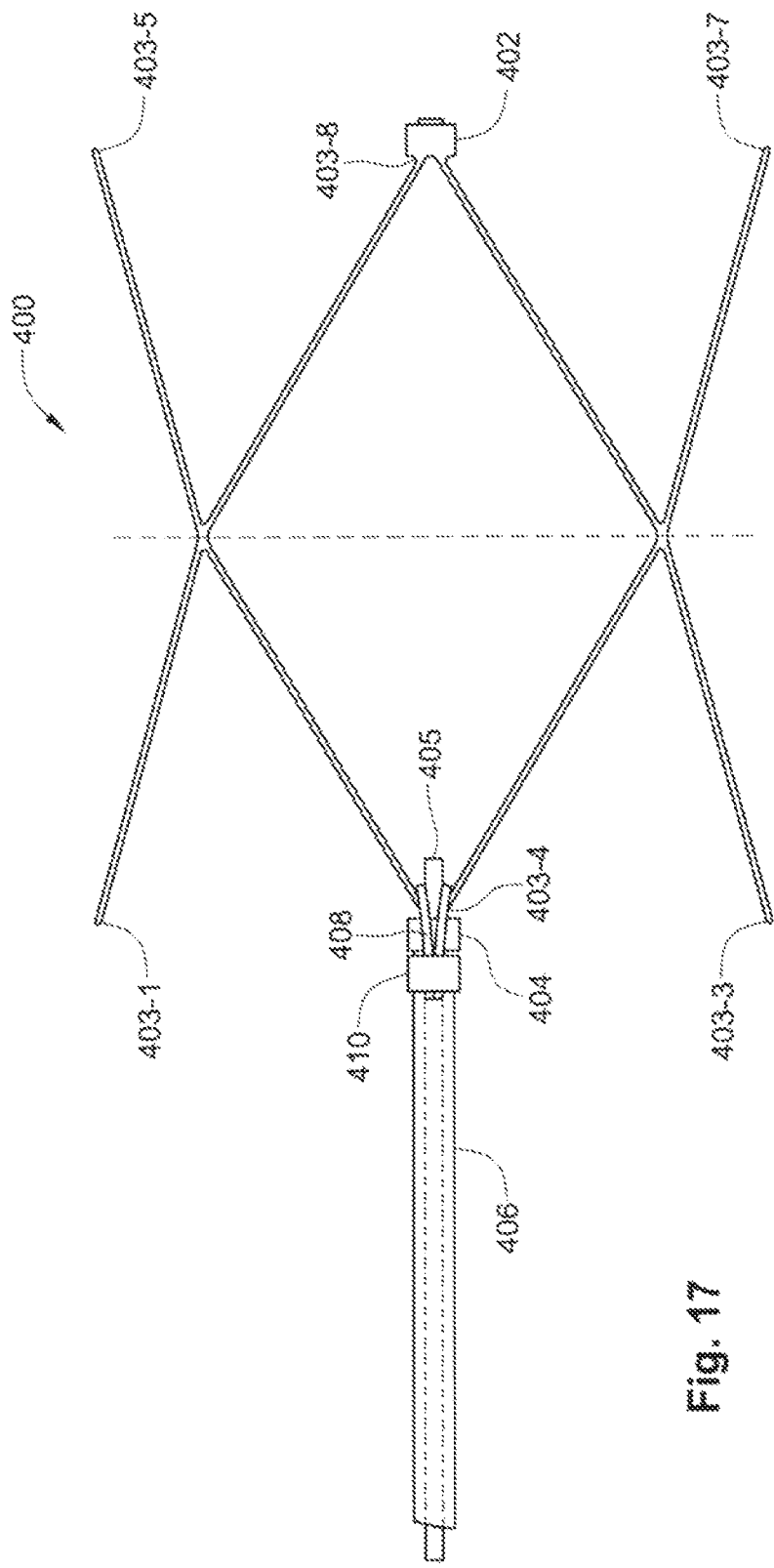

SYSTEMS, DEVICES, AND METHODS FOR DELIVERING A LUMEN OCCLUSION DEVICE USING DISTAL AND/OR PROXIMAL CONTROL

CROSS-REFERENCE TO RELATED APPLICATIONS

This application claims the benefit of U.S. Provisional Application Ser. No. 61/591,119 filed on Jan. 26, 2012 and U.S. Provisional Application Ser. No. 61/681,507 filed on Aug. 9, 2012, both of which are incorporated by reference herein in their entirety for all purposes.

STATEMENT REGARDING FEDERALLY SPONSORED RESEARCH OR DEVELOPMENT

This technology was developed with sponsorship by the National Science Foundation's AAA Endograft PII/IIB Grant No. 0823015 and the U.S. federal government has certain rights to this technology.

TECHNICAL FIELD

The present description relates generally to implantable devices for therapeutic treatment, and more particularly to an apparatus for endoluminally delivering a device for vascular occlusion.

BACKGROUND

During many clinical procedures, a physician requires the reduction or complete stoppage of blood flow to a target region of the patient's body to achieve therapeutic benefit. A variety of devices are available to provide occlusion of blood vasculature including embolic coils, metal-mesh vascular plugs, beads, particles, and glues. Interventional radiologists and vascular surgeons (and similar medical specialists) draw from these choices based upon the specific need and confidence of a rapid and effective occlusion given the attributes and deficiencies of each of these options. These devices may be used to occlude vasculature in situations, for example, requiring treatment of arteriovenous malformations (AVMs), traumatic fistulae, some aneurysm repair, uterine fibroid, and tumor embolization. For these clinical treatments, the blood flow through a target section of a blood vessel must be stopped. The device is introduced into the blood vessel through a sterile delivery catheter or sheath using common percutaneous access outside the body. The delivered, artificial device, induces an initial reduction of blood flow through a simple mechanical blockage which in turn triggers the body's natural clotting process to form a more complete blockage comprised of the thrombus adhered to the device.

Current exemplary embolic coils are made from biocompatible materials, and provide a biodurable, stable blockage of blood flow. The coils anchor to the vessel wall through radial compliance pressing onto the vessel wall surface. Coils must be suitably anchored to avoid migrating downstream under the forces of the blood flow, which can be significant in larger vasculature. Embolic coils are often shaped for flexibility through the use of a primary coiling, and for achieving a "coil pack" within the vessel through the use of a secondary, sometimes complex, three dimensional shape. The coil pack appears as a relatively random crossing and intertwining of the coil within the vessel. After slowing the blood flow, over time, a clot forms around the embolic coil, and blood flow through the section is completely blocked.

Typical embolic coils are formed using two major steps: 1) a wire of platinum or other bio-compatible material is wound into a spring, forming what is commonly referred to as a primary coil; and 2) the primary coil is in turn wound around a mandrel having a more complex shape and then subjected to high heat (e.g., heat setting) to yield a secondary coil. The secondary coil thus is a coiled wire of complex-shape or, if helical, a larger curl diameter. Coils can also be provided in other secondary shapes, such as those having multiple helical curl diameters, and in tapered helical shapes with one end employing a large curl diameter and the other end a small curl diameter. These metal coils are straightened, within their elastic bending limit, so as to be advanced into a delivery catheter and pushed down the catheter by a guide wire, pusher, or a detachable pre-attached pusher, until expelled into the vessel. Often, polymeric fibers are applied to the metallic coils in order to increase a thrombus response in addition to providing a scaffolding for thrombi to adhere to and be retained on the coil.

Embolic coils are sized to fit within the inner lumen of a catheter or sheath to be delivered to the target occlusion site individually and sequentially. Typically, a physician will use multiple coils to occlude a single vessel and in some cases, especially for larger blood vessels (above 5 mm or so), the physician may use a significant number coils to achieve cessation of blood flow. To complete an occlusion procedure with embolic coils, the physician must sequentially reload the catheter with several individual coils until he/she has determined that the occlusion is sufficient. The physician typically determines whether sufficient coils have been deployed by assessing the level of occlusion of the vessel flow, e.g., by using contrast media in concert with typical medical imaging techniques. This "place and assess" method can extend the medical procedure time, expose the patient to increased levels of contrast agent, and increase radiation exposure to both the patient and the physician through extensive imaging.

Embolic coils are also known for challenges in achieving precise vascular placement. Many of these coils are simply pushed out of the end of a delivery catheter. The final coil pack location is dependent upon whether the coil has been properly sized prior to deployment or whether the coil was properly anchored into a side vessel/branch as prescribed by several of the coil manufacturers for greater confidence in the coil pack's final position. Both of these techniques require a high level of physician skill if there is a desire to accurately position both the distal and proximal faces of the coil pack in a vessel using sequential, pushable coils. Some of the coil manufacturers provide a detachable coil that, once properly placed, can be released from a delivery control wire at the user's discretion. If the coil is not in the preferred location, it can be retracted and replaced if needed to achieve better position. However, only the proximal end of the coil is attached to this control wire resulting in only indirect control of the position of the coil pack's distal face.

Using coils for embolization can present other unique challenges. Voids in the coil pack, developed either during the procedure or post operatively, can cause channels and resulting blood flow in an unintended area. This condition is typically referred to as recanalization. Depending upon the significance of the condition, e.g., internal hemorrhage, retreatment or surgical intervention may be necessary. The ability to quickly and reliably develop a consistently dense coil pack in a vessel is a key to a successful vascular occlusion product.

Also, embolic coils can be easily misplaced. Embolic coils may either be injected through a delivery catheter with a syringe filled with saline, pushed by an independent guide wire, or deployed with a detachable pusher that is only connected to the coil via its proximal end. The coil pack shape is dependent upon the successful placement of the initial coil. Therefore, coils can easily be misplaced, should the initial coil not land correctly or be slightly undersized to the target vessel and slip beyond the target location. As such, embolic coil packs are known for a high propensity of being elongated in overall size. While these devices have been employed clinically for years, coils reflect significant challenges when attempting to embolize in a very precise or limited section of vasculature.

Metal mesh vascular plug devices have also been developed and commercialized to achieve vascular occlusion. These devices achieve occlusion with a single deployment using a metal mesh to provide mechanical flow blockage and, after some time, a thrombus forms and a complete occlusion results. When deployed, these devices appear like metal mesh balloons or baskets, with one or more lobes contacting the vascular wall, but with defined proximal and distal faces. With occlusion occurring after a single device deployment, these products address many of the deficiencies of embolic coils. However, due to the porosity of the mesh basket and the lack of the polymeric fibers used in coils, the metal mesh plugs have been shown to take longer to achieve occlusion than a properly placed embolic coil pack.

Further, these metal mesh devices are relatively stiff due to their construction and have limited ability to traverse the sharp turns found in catheters that have been placed in a highly tortuous vascular path. The mesh is collapsed into a narrow tube-like shape for introduction and deployment through a delivery catheter or sheath before expanding into the balloon-like shape upon deployment. This narrow tube-like shape allows the device to be delivered in the central lumen of small catheters or sheaths similar to coils. However, when the mesh is collapsed, it elongates and becomes a fairly rigid tubular structure. So while being capable of entry into a small delivery catheter, it has a limited ability to traverse the sharp turns found in highly tortuous paths to the target vessel. Subsequently, the advantages of a single occlusion device are offset by the slow occlusion performance and limited application to occlusion target sites that have non-tortuous access.

The information included in this Background section, including any references cited herein and any description or discussion thereof, is included for technical reference purposes only and is not to be regarded subject matter by which the scope of the claims is to be bound.

SUMMARY

In one embodiment a delivery apparatus for distal and proximal control of a vascular or lumen occlusion device is disclosed. Example applications for the vascular occlusion device include, but are not limited to, the occlusion of peripheral vasculature, occlusion of cerebral aneurysms, and the occlusion of parent vessels to cerebral aneurysms. An exemplary occlusion device controlled by the delivery apparatus includes a plurality of coil members, with each member defining a proximal end and a distal end. The occlusion device also includes a proximal retaining feature coupled to the proximal ends of the plurality of coil members and a distal retaining feature coupled to the distal ends of the plurality of coil members. The proximal and distal retaining features may each be a nubbin (e.g., a homogenous section formed by the coil material, adhesive, etc.). The delivery apparatus may include a pusher configured for moving the proximal retaining feature in a distal direction, or both proximal and distal directions, and a distal control wire releasably coupled to the distal retaining feature. The distal control wire may be configured for moving the distal retaining feature in both proximal and distal directions.

In some embodiments, the occlusion device may be delivered within the vasculature by the delivery apparatus within a delivery catheter. In additional embodiments, the distal control wire extends through the proximal retaining feature and the pusher, which may both move freely relative to the distal control wire and the distal retaining feature. In further embodiments, the distal control wire may be decoupled from the distal retaining feature by applying a force on the wire in a proximal direction that is greater than a minimum threshold force.

The disclosed vascular or lumen occlusion apparatus (or system) allows for controlling both the proximal and distal ends of the occlusion device, thereby enhancing the delivery, placement, packing density, and anchoring of the occlusion device within a vessel, which are key characteristics of a successful embolic procedure. Existing single coil devices, whether pushable or detachable (i.e., where the occlusion devices are held/detached from only their proximal end), rely on the curl or shape of the coil members to control the distal position of the occlusion device and are typically anchored to the closest or immediate vessel wall upon exiting the delivery catheter. During and after deployment of the occlusion device, the coil members may migrate downstream (distally) to an unintended location along the vessel.

The disclosed delivery apparatus allows for controlling the distal end throughout the delivery of the occlusion device in the delivery catheter, as well as during deployment of the device in the vessel. This allows the attending physician to maintain the occlusion device in a specific position relative to the delivery catheter until the point of release, resulting in more accurate placement of the occlusion device during the occlusion procedure and avoiding misplacement of the occlusion device within the lumen.

The distal end control provided by the disclosed delivery apparatus may further allow for more effective compression of the coil members between the distal and proximal retaining ends, resulting in the formation of a higher density coil pack. For example, the disclosed apparatus allows the attending physician to maintain the position of the distal end of the occlusion device while pushing the proximal end, thereby compressing the coil members between the proximal and distal ends. Alternatively, the distal end of the occlusion device may further be pulled in a proximal direction via the wire to further compress in the coil members. The disclosed occlusion apparatus thereby allows for better compression of the coil members, resulting in a higher-density coil pack with increased flow blockage and anchoring properties.

The disclosed delivery apparatus further allows for retaining the proximal end of the occlusion device with the pusher until it is specifically released by the physician. In other words, the apparatus allows the physician to control the position of the proximal end of the occlusion device as it is delivered through the catheter and during deployment. This feature provides multiple advantages. For example, it allows for positioning coil members in slight tension between the proximal and distal ends, thereby preventing bunching of the coil members as they are moved through the delivery catheter before deployment into the lumen, as well as preventing buckling of the individual coil members. Accordingly, damage to the coils during delivery of the occlusion device through the catheter is avoided and the force to pass the device through the delivery catheter is reduced.

The proximal control provided by the disclosed delivery apparatus further allows for repositioning of the occlusion device during the occlusion procedure. For example, the physician may retract a partially deployed occlusion device back into the delivery catheter, as well as remove a partially deployed occlusion device from the vessel without retracting it back into the delivery catheter. This feature serves to reduce the potential for leaving a misplaced occlusion device within the vessel, which may lead to other medical complications or require surgical intervention to correct.

The proximal and distal control provided by the disclosed delivery apparatus may be similarly beneficial if the occlusion device was a single coil device, and regardless of material, e.g., metals (stainless steel, platinum, nitinol), traditional polymers/plastics (thermoplastic or thermoset resins), shape memory polymers, or a combination of these. It can be seen that the benefits of such a delivery apparatus may also be applicable for use with devices for occlusion of any number of types of biological lumens, e.g., arterial and venous vasculature, reproductive tracts (e.g., fallopian tubes), lung and air passageways (including lung lobe resection), digestive organs (esophagus, stomach, intestines, bile ducts and other passageways in the biliary tree, etc.), left atrial appendages, patent foramen ovales, and so forth.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of relevant features, details, utilities, and advantages are provided in the following written description of various embodiments of the inventive subject matter and illustrated in the accompanying drawings.

BRIEF DESCRIPTION OF THE FIGURES

The details of the subject matter set forth herein, both as to its structure and operation, may be apparent by study of the accompanying figures. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 1A is a schematic side view of a distal end of an example embodiment of a vascular occlusion apparatus in a first stage, before deployment of the occlusion device.

FIG. 1B is a schematic cross-sectional view of the distal end of the vascular occlusion apparatus shown in FIG. 1A.

FIG. 2A is a schematic side view of the distal end of the vascular occlusion apparatus shown in FIG. 1A in a second stage, in which the distal retaining feature is advanced past the distal end of the delivery catheter.

FIG. 2B is a schematic side view in cross section of the distal end of the vascular occlusion apparatus shown in FIG. 1A in a third stage, in which a coil pack is formed.

FIG. 3A is a schematic side view in cross section of the distal end of the vascular occlusion apparatus shown in FIG. 1A in a fourth stage, in which the distal control wire is disconnected from the distal retaining feature.

FIG. 3B is a schematic side view in cross section of the distal end of the vascular occlusion apparatus shown in FIG. 1A in a fifth stage, in which the occlusion device is released into the vessel.

FIG. 4 is a schematic side view in cross section of an alternative embodiment of a distal end of a vascular occlusion apparatus with a distal control wire having an enlarged section to aid in retention of the proximal control wire.

FIG. 5 is a schematic side view in cross section of a distal end of another embodiment of a vascular occlusion apparatus with an additional lock wire interfacing with the ball on the end of the distal control wire.

FIG. 6 is a schematic side view in cross section of a distal end of another embodiment of a vascular occlusion apparatus with an additional lock wire and a proximal control wire extending proximally through the delivery catheter ex vivo.

FIG. 7A is a schematic isometric view of an alternate embodiment of a retention structure in the form of an elastomeric O-ring for retaining the distal end of the distal control wire within a distal engagement feature.

FIG. 7B is a schematic side view in cross section of the O-ring retention structure of FIG. 7A within the distal engagement feature.

FIG. 13C is a side view of an exemplary embodiment of the occlusion apparatus during release of the implant.

FIG. 13D is a perspective and partial cross-sectional view of an embodiment of a proximal retaining feature used in conjunction with another exemplary embodiment of the occlusion apparatus.

FIG. 16A is a side view of an exemplary embodiment of a stent in a radially expanded state.

FIG. 16B is a partial side view of the embodiment of the stent of FIG. 16B in a radially compressed state.

FIG. 17 is a side view of an exemplary embodiment of an embolic cage release system.

DETAILED DESCRIPTION

Figure 8:
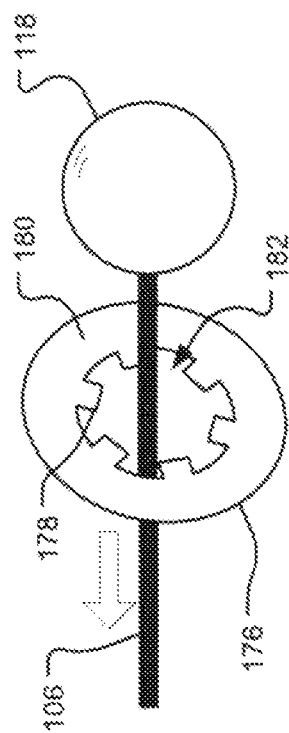
FIG. 8 is a schematic isometric view of another embodiment of a retention structure in the form of a C-clip for retaining the distal end of the distal control wire within a distal engagement feature.

This detailed description sets forth numerous embodiments of an occlusion apparatus. It should be noted that all features, elements, materials, components, functions, and steps described with respect to any embodiment of this occlusion apparatus (and methods of using and making the apparatus) are intended to be freely combinable and substitutable with those from any other embodiment. If a certain feature, element, component, function, or step is described with respect to only one embodiment, then it should be understood that that feature, element, material, component, function, or step can be used with every other embodiment described herein unless explicitly stated otherwise. This paragraph therefore serves as antecedent basis and written support for the introduction of claims, at any time, that combine features, elements, materials, components, functions, and steps from different embodiments, or that substitute features, elements, materials, components, functions, and steps from one embodiment with those of another, even if the following description does not explicitly state, in a particular instance, that such combinations or substitutions are possible.

Vascular sections targeted for occlusion may present with some anatomical variability. Therefore, a clinically acceptable vascular occlusion device is flexible and adaptive to the structure it is filling while anchoring without inducing significant pressure on the vessel wall to avoid migration under the influence of the blood flow. It should be noted that all example embodiments of occlusion implant devices described herein can be used with all embodiments of the delivery apparatus of portion of a delivery apparatus, unless explicitly stated otherwise. A delivery apparatus may deliver an occlusion device into a vessel or lumen wherein the occlusion device is constructed of one or a series of (preferably parallel) coil members. For instance, in one embodiment, the occlusion device has seven coil members and fits in a sheath (or delivery catheter) that has an approximately 5 French (Fr) inner diameter (ID). In another embodiment for a sheath ID larger than 5 Fr, the occlusion device has more than seven coil members (e.g., 8, 9, 10, etc.). In yet another embodiment for a sheath ID less than 5 Fr, the occlusion device has less than seven coil members (e.g., 1, 2, 3, 4, 5, or 6). It should be noted that this is only an example and that devices for larger than 5 Fr IDs may have seven or less coil members and devices for smaller than 5 Fr IDs may have seven or more coil members.

For the sake of clarity, it should also be noted that the occlusion device (e.g., proximal and distal hubs, coil members, etc.) can be fabricated from any metallic material (e.g., stainless steel, platinum, nitinol and other nickel-titanium alloys, and so forth), polymeric material (e.g., PEEK, plastics (thermoplastic or thermoset resins), shape memory polymers, and so forth), or a combination of both.

The coil members may be delivered simultaneously to form a coil pack to occlude a vascular target. The occlusion device may be used, for example, for occluding an artery or vein, to block blood flow within a vessel supplying blood to or from the liver (hepatic artery), kidney (renal artery), spleen (splenic artery) or intestines (mesenteric artery), but not limited to these applications. Occlusion devices may also be used for occlusion of other biological lumens, for example, reproductive tracts (e.g., fallopian tubes), lung and air passageways (including lung lobe resection), digestive organs (esophagus, stomach, intestines, bile ducts and other passageways in the biliary tree, etc.), left atrial appendages, patent foramen ovales, and so forth.

A delivery apparatus that delivers the occlusion device into a vessel or other biological lumen may include a distal control wire for controlling a distal end of the occlusion device and a pusher or a separate proximal control wire for manipulating the proximal end of the occlusion device. The coil members of the occlusion device may be joined together at the distal end to provide greater control of the resulting coil pack, reduce the potential for errant coils to extend downstream in the vessel, and facilitate the ability to utilize a distal control wire. The distal retaining feature may be releasably coupled to the distal control wire, which allows the distal retaining feature to be controlled during delivery of the vascular occlusion device and to be released at the proper time within the vessel. The coil members of the occlusion device may be joined together at the proximal end to provide greater control of the occlusion device during delivery, provide greater control of the resulting coil pack, reduce the potential for errant coils to prolapse upstream adjacent to the catheter in the lumen, and facilitate the ability to utilize a pusher that is releasably coupled to the proximal end of the occlusion device. The proximal retaining feature may be releasably coupled to the pusher, which pushes the proximal retaining feature through the catheter. The disclosed design, which allows for both proximal and distal end control of the vascular or lumen occlusion device, helps reduce the delivery force and guide the occlusion device into proper placement in the lumen, and further allows for better compression of the coil members to form a higher density coil pack.

FIGS. 1A and 1B illustrate an occlusion apparatus 100 in a first preliminary stage, before deployment of an occlusion device. As is shown, the occlusion apparatus 100 may include an occlusion device 108, a pusher 104, a proximal coupling wire 156, and a distal control wire 106 that are housed within a sheath or delivery catheter 102. The occlusion device 108 may include a plurality of coil members 114 which are joined at their respective proximal and distal ends 123, 125 by a proximal retaining feature 110 and a distal retaining feature 112, which are each shown here to be configured as hubs. As shown in FIGS. 1A and 1B, the coil members 114 are in an elongated, predeployment state for delivery through the catheter 102. The pusher 104 may engage the proximal end of the proximal retaining feature 110 to push the proximal retaining feature 110 in a distal direction through the delivery catheter 102.

In one embodiment, a short segment of wire with a ball end feature, i.e., the proximal coupling wire 156 with a lock ball 154, is attached to the distal end of the pusher 104 within a sidewall of an internal passage 122 defined within the pusher 104. The proximal retaining feature 110 provides an internal passage 120 with a larger diameter section providing a retention chamber 152 in which the lock ball 154 of the proximal coupling wire 156 resides after assembly. Both the proximal coupling wire 156 and the distal control wire 106 pass through the internal passage 120 in the proximal retaining feature 110. With both wires 106, 156 passing through the internal passage 120, the proximal lock ball 154 is inhibited from pulling free of the retention chamber 152 within the proximal retaining feature 110. Upon detachment, detailed below, the distal control wire 106 is retracted through the proximal retaining feature 110. With the distal control wire 106 completely withdrawn, there is sufficient clearance for the proximal coupling wire 156 and lock ball 154 to release from the retention chamber 152 in the proximal retaining feature 110.

The distal control wire 106 may be releasably coupled to the distal retaining feature 112 such that the distal retaining feature 112 is positioned by the physician and then held approximately 1.5 to 2 cm past the distal end of the delivery catheter 102. In one embodiment, the distal control wire 106 may be a metal wire, such as a stainless steel or nitinol wire. As best shown in FIG. 1B, the distal control wire 106 may extend from the proximal end of the distal retaining feature 112 through internal passages 120, 122 defined by the proximal retaining feature 110 and the pusher 104, respectively. The distal control wire 106 may or may not contact the proximal retaining feature 110 and pusher 104, which are allowed to move freely in proximal and distal directions relative to the distal wire 106 and the connected distal retaining feature 112.

In some embodiments, the proximal and distal retaining features 110, 112 may be a molded nubbin or other structure that permanently joins the respective proximal and distal ends of the coil members 114. In another exemplary embodiment, the ends of the coil members may be permanently held together via a metal band, tie, wrap, or crimp. The retaining features 110, 112 of the occlusion device 100 may be made from other biocompatible materials, for example polyetheretherkeytone (PEEK), to provide high dimensional capabilities for the precision openings and access channels and may be bonded to the molded nubbin or exposed ends of the joined coil member 114. Other embodiments may utilize other configurations of retaining features 110, 112. For example, the proximal and distal ends 123, 125 may be bonded together by an adhesive, and the distal end of the wire 106 may be embedded in the adhesive joining the coil members 114 together. In another exemplary embodiment, the proximal and distal ends 123, 125 may be housed within a compressive cap and the distal end of the control wire 106 held therein by friction fit. A combination of two or more of each of these aforementioned options is also possible.

Referring to FIG. 1B, the distal retaining feature 112 may be configured to hold a stopper element 118, which may be dislodged from the distal retaining feature 112 through the application of a threshold force in the distal direction. The stopper element 118 (e.g. a stainless steel or Nitinol ball) may be joined to the distal end of the control wire 106 or, alternatively, the distal end of the control wire may be enlarged with respect to the control wire's shaft. In some embodiments, the distal retaining feature 112 may define or house an engagement feature 116 at or within a proximal end of the distal retaining feature 112 that engages the outer surface of the stopper element 118 to retain the stopper element 118 within the distal retaining feature 112. For example, the engagement feature 116 may have a narrow opening or access channel 150 through which the control wire 106 passes. The diameter of the outer surface of the stopper element 118 may be slightly larger than the diameter of the access channel 150. The access channel 150 may be somewhat pliable and the stopper element 118 can be dislodged from the distal retaining feature 112 by pulling the control wire 106 with sufficient force (i.e., the threshold force) to pull the stopper element 118 through the access channel 150 to overcome the engagement feature 116. Pulling the control wire 106 with less force than the threshold force will move the distal retaining feature 112 proximally or distally, but will not disconnect the control wire 106 from the distal retaining feature 112. In an alternate embodiment, the control wire 106 may disconnect from the stopper element 118 at the threshold force and the stopper element 118 may remain in the engagement feature 116 while the control wire 106 is withdrawn. In yet another embodiment, the stopper element 118 may be deformable, elastic, or pliable, such that it will change its shape and pass through the narrow opening or access channel 150 upon the application of the threshold force.

In other embodiments, the distal control wire 106 may be otherwise releasably joined to the distal retaining feature 112. For example, the distal end of the distal control wire 106 may be attached to the distal retaining feature 112 using an adhesive, and the distal control wire 106 may be dislodged from the wire 106 by applying sufficient force 138 in the proximal direction to break the adhesive bonds. Alternatively, the distal control wire 106 may be embedded in the distal retaining feature 112 and held therein by compression and friction, and the control wire 106 may be dislodged by applying a minimum threshold force required to remove the control wire 106 from the distal retaining feature 112. In an alternate embodiment, the distal end of the control wire 106 may be formed of a fiber, a weakened area, or smaller gauge of wire, and may be broken, such that the distal end of the distal control wire 106 remains within the distal retaining feature 112 as it is deployed in the vessel. Another embodiment may utilize a releasable clamp on the proximal end of the distal control wire 106 to releasably join the control wire 106 to the distal retaining feature 112.

FIG. 2A illustrates the apparatus 100 shown in FIGS. 1A and 1B in a second stage, in which the occlusion apparatus 100 is first inserted into vessel 124 deployed from the delivery catheter 102. In this stage, the proximal retaining feature 110 is advanced along the control wire 106 in a distal direction (represented by arrow 130) towards the distal end of the catheter 102. As discussed above, the proximal retaining feature 110 may be moved by the pusher 104 housed in the delivery catheter 102. The distal retaining feature 112 is simultaneously moved in a distal direction away from the catheter 102. As discussed above, the distal retaining feature 112 may be moved by pushing and pulling the control wire 106. During this second stage, the physician may move the distal retaining feature 112 in both proximal and distal directions (represented by bi-directional arrow 132) by manipulating the proximal end of the control wire 106, so long as the force applied to the stopper element 118 is not sufficient to dislodge the stopper element 118 from the distal retaining feature 112. The distal retaining feature 112 may be maintained at a constant separation distance from the proximal retaining feature 110 via the control wire 106 during travel through the catheter 102 such that the coil members 114 retain their linear (e.g., generally straight) shape, may be placed under slight tension, and are oriented in a substantially parallel configuration to minimize delivery friction and force. This feature allows for deployment of coil structures that may not have sufficient tensile strength in an elongated form to navigate a catheter 102 without buckling and possibly getting stuck.

After the occlusion device 108 has been extended beyond the delivery catheter 102 a prescribed distance as controlled by the physician, the distal control wire 106 may be restricted from further movement, thereby holding the distal retaining feature 112 of the occlusion device 108 in a stable position. Deployment of the occlusion device 108 continues by further advancing the pusher 104.

A comparison of the device 100 in FIG. 2A with the device 100 in FIGS. 1A and 1B shows that the distance between the proximal and distal retaining features 110, 112 decreases in the second stage as the coil members 114 begin to curl at the distal end upon deployment. FIG. 2B illustrates the apparatus 100 in a third stage, in which both the proximal and distal retaining features 110, 112 are in the vessel 124 and a coil pack 126 is formed. A comparison of FIG. 2B with FIG. 2A reveals that the pusher 104 has advanced the proximal retaining feature 110 along the control wire 106 past the distal end of the catheter 102, while the distal retaining feature 112 is maintained in the same position within the vessel 104 as in the second stage (shown in FIG. 2A), further decreasing the distance between the proximal and distal retaining features 110, 112. During this stage, the coil members 114 deploy and change from an elongated form to a curled form, and are further compressed, thereby forming a dense coil pack 126 between the proximal and distal retaining features 110, 112. As discussed above, maintaining the distal retaining feature 112 in a fixed position may allow for better compression of the coil members 114 against the distal retaining feature 112 as the pusher 104 is advanced towards the distal retaining feature 112, thereby increasing the density and outward radial force of the resulting coil pack 126 which increases flow blockage and therefore reduces occlusion time. Similar to the second stage shown in FIG. 2A, at the physician's discretion, the distal retaining feature 112 may still be moved in both proximal and distal directions 132 as shown in FIG. 2B by manipulating the proximal end of the control wire 106 ex vivo, allowing the attending physician to accurately position the occlusion device 108 during the occlusion procedure such that it will be anchored in an appropriate location within the vessel 124.

At this third stage, in which the distal retaining feature 112 is still connected to the control wire 106, the physician can freely retract a partially deployed occlusion device back into the delivery catheter 102, if necessary, by pulling the pusher 104 and the proximal control wire 156 in a proximal direction, drawing the coiling members 114 back into the delivery catheter 102. The entire occlusion device 108 may be retracted until the distal control wire 106 and the distal retaining feature 112 are retracted back into the catheter 102. This reduces the potential for having to leave a misplaced occlusion device 108 within the vessel 124, which may lead to other medical complications or require surgical intervention to correct. Alternatively, the physician may choose to remove the partially deployed occlusion device 108 from the vessel 124 without retracting into the catheter 102 by simply removing the occlusion device 108 and the delivery catheter 102 simultaneously while the occlusion device 108 remains connected to the proximal coupling wire 156 and/or the distal control wire 106 within the proximal and distal retaining features 110, 112, respectively.

FIG. 3A illustrates the apparatus 100 in a fourth stage, in which the stopper element 118 is dislodged from the engagement feature 116 of the distal retaining feature 112. As discussed above, removal of the stopper element 118 may require an application of a threshold force in the proximal direction (represented by arrow 138) on the control wire 106 that is sufficient to overcome any compression, adhesion, or frictional forces applied by the engagement feature 116 on the surface of the stopper element 118. Applying a force that is smaller than the threshold force will serve to move the distal retaining feature 112 in a proximal or distal direction (represented by arrow 132 in FIGS. 2A and 2B), as described above with respect to FIGS. 2A and 2B.

The stopper element 118 may have a spherical shape, as shown, or may have some other low friction shape which does not have sharp corners or edges which might catch and potentially damage the coil members 108 defining the coil pack 126 as it is withdrawn. As described above in other embodiments, the control wire 106 may disengage from the stopper element 118 or otherwise separate from the distal retaining feature 112 and be withdrawn through the coil pack 126 and into the catheter 102.

FIG. 3B illustrates the occlusion apparatus 100 in a fifth stage, in which the occlusion device 108 has been released within the vessel 124. As is shown, the stopper element 118 is pulled in a proximal direction (represented by arrow 140) via the control wire 106 and drawn through the coil pack 126 and the passage 120 defined by the proximal retaining feature 110 back into the catheter 102. In this stage, the control wire 106 and stopper element 118 are completely disconnected from the occlusion device 108, which is anchored within the vessel 124. Once the stopper element 118 passes through the proximal retaining feature 110 and is retracted into the passage 122 defined by the pusher element 104, the lock ball 154 and proximal control wire 156 are released from the proximal retaining feature 110. The pusher element 104 and the catheter 102 may then be removed from the lumen 124.

FIG. 4 illustrates an alternative embodiment of an occlusion apparatus 400 in a preliminary stage, before deployment of the occlusion device 108. As in previous embodiments, the occlusion apparatus 400 may include the occlusion device 108, a pusher 104, a proximal coupling wire 156, and a distal control wire 106 that are housed within a sheath or delivery catheter 102. The occlusion device 108 may include a plurality of coil members 114 which are joined at their respective proximal and distal ends 123, 125 by a proximal retaining feature 110 and a distal retaining feature 112. As in the prior embodiment, a short segment of wire with a ball end feature, i.e., the proximal coupling wire 156 with a lock ball 154, is shown attached to the distal end of the pusher 104 within a sidewall of an internal passage 122 defined within the pusher 104. The proximal retaining feature 110 provides an internal passage 120 with a larger diameter section providing a retention chamber 152 in which the lock ball 154 of the proximal coupling wire 156 resides after assembly. Both the proximal coupling wire 156 and the distal control wire 106 pass through the internal passage 120 in the proximal retaining feature 110. In another embodiment, the proximal coupling wire 156 may be attached to the end of the pusher 104.

In this embodiment, the distal control wire 106 may have a stepped diameter with a proximal portion 160 being of a larger diameter than a distal portion 162 of the distal control wire 106 attached to the lock ball 118. During deployment, the proximal portion 160 may extend beyond the end of the pusher 104 to an intermediate point within the occlusion device 108. With both wires 106, 156 passing through the internal passage 120, the proximal lock ball 154 is inhibited from pulling free of the retention chamber 152 within the proximal retaining feature 110. The thicker proximal portion 160 of the distal control wire 106 is adjacent to the proximal lock ball 154 to help ensure that the proximal lock ball 154 maintains the engagement with the proximal retaining feature 110 of the occlusion device 108. When the distal control wire 106 is pulled proximally, the thicker proximal portion 160 is pulled past the proximal lock ball 154. The length of the thinner distal portion 162 of the distal control wire 106 may be chosen such that the thicker proximal portion 160 remains in contact with the proximal lock ball 154 for a significant portion of the linear contraction of the occlusion device 108 as the coil members 114 coil to ensure that the proximal end of the occlusion device 108 remains in place and the proximal lock ball 154 does not release too early.

The precision dimensions of the components may be designed to allow the proximal lock ball 154 to disengage from the retention chamber 152 in the proximal retaining feature 110 as the thinner distal portion 162 passes by the proximal lock ball 154 (i.e., the retention chamber 152 is designed such that there is enough clearance for the distal portion 162 of the distal control wire 106 and the proximal lock ball 154 to exit the proximal retaining feature 110). Thus, with the proximal lock ball 154 removed, it is easier (i.e., a lower force is required) for the distal lock ball 118 to pass through the proximal retaining feature 110 because it does not have to pass the proximal lock ball 154.

FIG. 5 illustrates another alternative embodiment of an occlusion apparatus 500 in a preliminary stage, before deployment of the occlusion device 108. As in previous embodiments, the occlusion apparatus 500 may include the occlusion device 108, a pusher 104, a proximal coupling wire 156, and a distal control wire 106 that are housed within a sheath or delivery catheter 102. The occlusion device 108 may include a plurality of coil members 114 which are joined at their respective proximal and distal ends 123, 125 by a proximal retaining feature 110 and a distal retaining feature 112. As in the prior embodiments, a short segment of wire with a ball end feature, i.e., the proximal coupling wire 156 with a lock ball 154, is attached to the distal end of the pusher 104. The proximal retaining feature 110 provides an internal passage 120 with a larger diameter section providing a retention chamber 152 in which the lock ball 154 of the proximal coupling wire 156 resides after assembly. Both the proximal coupling wire 156 and the distal control wire 106 pass through the internal passage 120 in the proximal retaining feature 110.

In this embodiment, a lock wire 164 is used in conjunction with the distal control wire 106. The lock wire 164 may extend (or be coextensive) with the distal control wire 106 from a delivery control system located proximally ex vivo to the termination in the distal retaining feature 112. Both the distal control wire 106 and the lock wire 164 are thus controlled by the physician. When the lock wire 164 is in place within the distal retaining feature 112, there is insufficient clearance through the access channel 150 for the lock ball 118 to pass, i.e., the lock ball 118 is retained by an interference fit. Additionally, the combined diameters of the distal control wire 106 and the lock wire 164 adjacent to the proximal lock ball 154 help ensure that the proximal lock ball 154 maintains the engagement with the proximal retaining feature 110 of the occlusion device 108.

When time for detachment, the lock wire 164 may be retracted proximally and removed from the distal retaining feature 112. Further, in this embodiment, there is no need for the access channel 150 to be a precision dimension component; the diameter of the access channel 150 may actually be slightly larger than the diameter of the distal lock ball 118, thereby allowing the distal lock ball 118 to easily exit the distal retaining feature 112 without additional force. Depending upon the cross-sectional dimensions of the lock wire 164 and the distal control wire 106, the proximal lock ball 154 may remain in place in the proximal retaining feature 110 after the lock wire 164 is retracted through the proximal retaining feature 110 or the proximal lock ball 154 may dislodge from the proximal retaining feature 110 once the lock wire 164 is retracted through the proximal retaining feature 110. In the former case, the occlusion device 108 will remain attached to the pusher 104 until the distal lock ball 118 passes by the proximal lock ball 154 in the retention chamber 152. In the latter case, once the lock wire 164 exits the proximal retaining feature 110, the precision dimensions of the components may be designed to allow the proximal lock ball 154 to disengage from the retention chamber 152 as there is enough clearance for the proximal lock ball 154 to exit the proximal retaining feature 110 adjacent the distal control wire 106. Again, if the proximal lock ball 154 is removed first, it may be easier for the distal lock ball 118 to pass through the proximal retaining feature 110 because it does not have to pass the proximal lock ball 154. Further, the physician may thus be provided greater control over when the proximal end of occlusion device 108 is released from the pusher 104.

FIG. 6 illustrates a further embodiment of an occlusion apparatus 600 in a preliminary stage, before deployment of the occlusion device 108. As in previous embodiments, the occlusion apparatus 600 may include the occlusion device 108, a pusher 104, a proximal coupling wire 158, and a distal control wire 106 that are housed within a sheath or delivery catheter 102 or, in the case of wires 158 and 106, may be housed within the pusher 104. The occlusion device 108 may include a plurality of coil members 114 which are joined at their respective proximal and distal ends 123, 125 by a proximal retaining feature 110 and a distal retaining feature 112. Unlike the prior embodiments, the proximal coupling wire 158 is not attached to the pusher 104, but instead extends all the way through the delivery catheter 102. The lock ball 154 is attached to the distal end of the proximal coupling wire 158. The proximal retaining feature 110 provides an internal passage 120 with a larger diameter section providing a retention chamber 152 in which the lock ball 154 of the proximal coupling wire 158 resides after assembly. Both the proximal coupling wire 158 and the distal control wire 106 pass through the internal passage 120 in the proximal retaining feature 110.

In this embodiment, the lock wire 164 is also used in conjunction with the distal control wire 106 in the same manner as previously described with respect to FIG. 5. Thus, all three wires, the distal control wire 106, the lock wire 164, and the proximal coupling wire 158 may extend (or be coextensive) with the distal control wire 106 from a delivery control system ex vivo for control by the physician. When the lock wire 164 is in place within the distal retaining feature 112, there is insufficient clearance through the access channel 150 for the lock ball 118 to pass. Additionally, the combined diameters of the distal control wire 106 and the lock wire 164 adjacent to the proximal lock ball 154 help ensure that the proximal lock ball 154 maintains the engagement with the proximal retaining feature 110 of the occlusion device 108. It may be noted that the proximal control wire 158 of this embodiment may be substituted for the proximal control wire 156 attached to the pusher 104 in prior embodiments.

When time for detachment, the lock wire 164 may be retracted proximally and removed from the distal retaining feature 112. Further, in this embodiment, there is no need for the access channel 150 to be a precision dimension component; the diameter of the access channel 150 may actually be slightly larger than the diameter of the distal lock ball 118, thereby allowing the distal lock ball 118 to easily exit the distal retaining feature 112 without additional force. Depending upon the cross-sectional dimensions of the lock wire 164 and the distal control wire 106, the proximal lock ball 154 may remain in place in the proximal retaining feature 110 after the lock wire 164 is retracted through the proximal retaining feature 110 or the proximal lock ball 154 may dislodge from the proximal retaining feature 110 once the lock wire 164 is retracted through the proximal retaining feature 110. In the former case, the occlusion device 108 will remain attached to the pusher 104 until the distal lock ball 118 passes by the proximal lock ball 154 in the retention chamber 152. In the latter case, once the lock wire 164 exits the proximal retaining feature 110, the precision dimensions of the components may be designed to allow the physician to retract the proximal control wire and disengage the proximal lock ball 154 from the retention chamber 152 as there is enough clearance for the proximal lock ball 154 to exit the proximal retaining feature 110 adjacent the distal control wire 106.

Again, if the proximal lock ball 154 is removed first, it may be easier for the distal lock ball 118 to pass through the proximal retaining feature 110 because it does not have to pass the proximal lock ball 154. Further, the physician may thus be provided greater control over when the proximal end of occlusion device 108 is released from the pusher 104.

FIGS. 7A and 7B depict an alternate exemplary implementation of an interface structure between the distal control wire 106 and the engagement feature 116 in the distal retaining feature 112. In this embodiment, instead of using a precision aperture for the access channel 150, the diameter of the access channel 150 is oversized to allow clearance around the lock ball 118. To provide the desired force for release of the distal control wire 106 from the distal retaining feature 112, an elastomeric O-ring 170 may be used. The O-ring 170 may be positioned within the engagement feature 116 and around the distal control wire 106. The outer diameter of the O-ring 170 is larger than the diameter of the access channel 150, thereby preventing the O-ring 170 from exiting the engagement feature 116. The inner diameter of the O-ring 170 is smaller than the diameter of the lock ball 118 on the control wire 106 so that the distal lock ball 118 is retained within the engagement feature 116. The size of the inner diameter, the wall thickness, and the material properties (e.g., hardness, modulus of elasticity) of the O-ring 170 may be chosen in conjunction with the size of the access channel 150 to provide for the O-ring 170 to radially expand under a specific force to allow the lock ball 118 to pass through the O-ring 170 for release of the distal control wire 106 from the distal retaining feature 112. As an alternative to an O-ring, a section of tubing can be used.

Figure 12A:
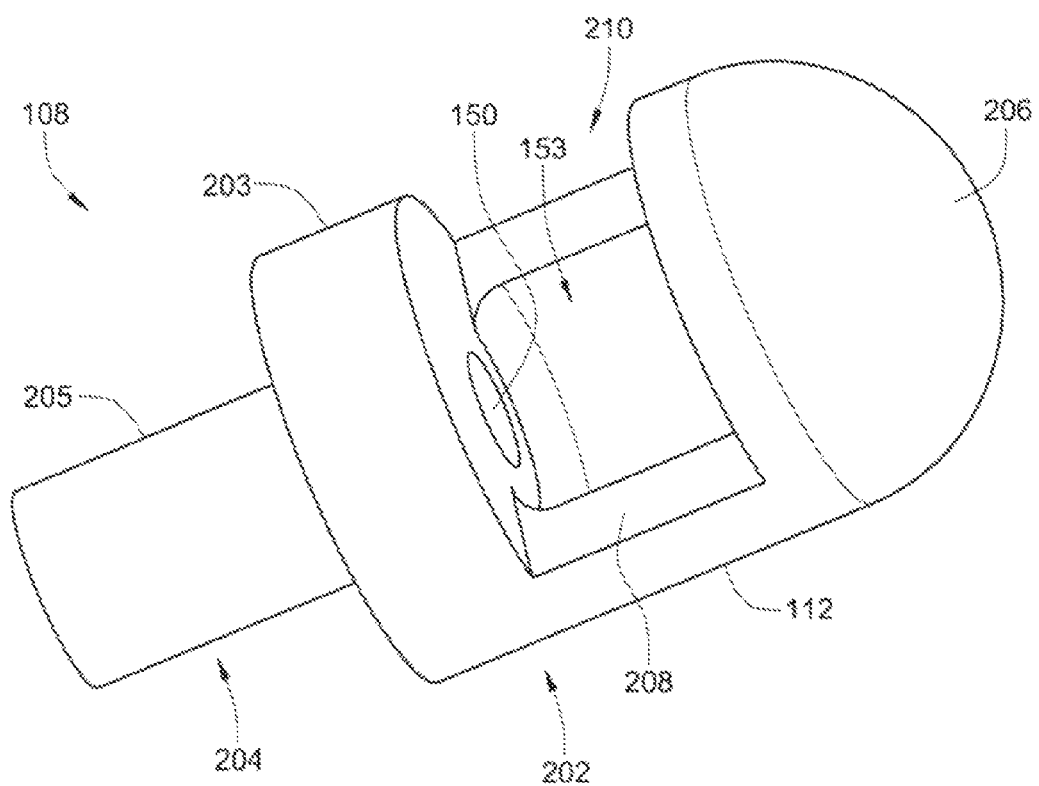
FIGS. 12A-B are perspective views of an exemplary embodiment of a distal retaining feature used in conjunction with an exemplary embodiment of the occlusion apparatus.

In order to assemble the device, the distal control wire 106 can be inserted into the distal retaining feature 112 through the access channel 150, and the O-ring or tubing can then be placed around the distal control wire 106, for instance, through a gap (or window) in the distal retaining feature 112 such as described with respect to FIG. 12A. The stopper element 118 can then be coupled to the distal terminus of the distal control wire 106 to lock the wire in place with respect to the distal retaining feature 112, at which point the gap (or window) can be optionally covered (such as with an insert) or otherwise blocked or filled in.

FIG. 8 depicts another exemplary implementation of an interface structure between the distal control wire 106 and the engagement feature 116 in the distal retaining feature 112. In this embodiment, a precision aperture for the access channel 150 is also not required and the diameter of the access channel 150 may be oversized to allow clearance around the lock ball 118. To provide the desired force control for release of the distal control wire 106 from the distal retaining feature 112, a C-clip or split washer (or ring) 172 defining a gap 174 in the circumference of the split washer 172 may be used. The split washer 172 may be positioned within the engagement feature 116 and around the distal control wire 106. The outer diameter of the split washer 172 is larger than the diameter of the access channel 150, thereby preventing the split washer 172 from exiting the engagement feature 116. The inner diameter of the split washer 172 is smaller than the diameter of the lock ball 118 on the control wire 106 so that the distal lock ball 118 is retained within the engagement feature 116. The size of the inner diameter, the width of the gap 174, and the material properties (e.g., tensile and shear strength of metal, plastic, or other material used to form the) of the split washer 172 may be chosen in conjunction with the size of the access channel 150 to provide for the split washer 172 to bend and widen the gap 174 under a specific force to allow the lock ball 118 to pass through the split washer 172 for release of the distal control wire 106 from the distal retaining feature 112.

Figure 9:
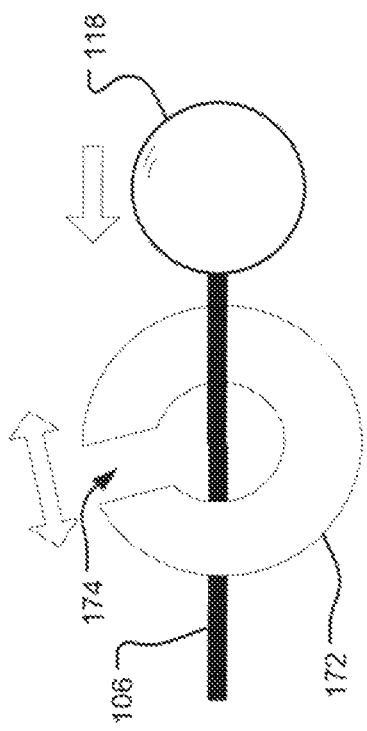
FIG. 9 is a schematic isometric view of another embodiment of a retention structure in the form of a star washer for retaining the distal end of the distal control wire within a distal engagement feature.

FIG. 9 depicts a further exemplary implementation of an interface structure between the distal control wire 106 and the engagement feature 116 in the distal retaining feature 112. In this embodiment, a precision aperture for the access channel 150 is not required and the diameter of the access channel 150 may be oversized to allow clearance around the lock ball 118. To provide the desired force control for release of the distal control wire 106 from the distal retaining feature 112, a star washer (or ring) 176 having a plurality of tabs 178 extending radially inward from a ring portion 180 into an aperture 182 of the star washer 176 may be used. The star washer 176 may be positioned within the engagement feature 116 and around the distal control wire 106. The outer diameter of the star washer 176 is larger than the diameter of the access channel 150, thereby preventing the star washer 176 from exiting the engagement feature 116. The inner diameter of the star washer 176 measured from the ends of the tabs 178 is smaller than the diameter of the lock ball 118 on the control wire 106 so that the distal lock ball 118 is retained within the engagement feature 116. The size of the inner diameter and the material properties (e.g., tensile and shear strength of metal, plastic, or other material used to form the star washer 176) of the star washer 176 may be chosen in conjunction with the size of the access channel 150 to provide for the tabs 178 of the star washer 176 to bend and widen the aperture 182 under a specific force to allow the lock ball 118 to pass through the star washer 176 for release of the distal control wire 106 from the distal retaining feature 112.

Figure 10:
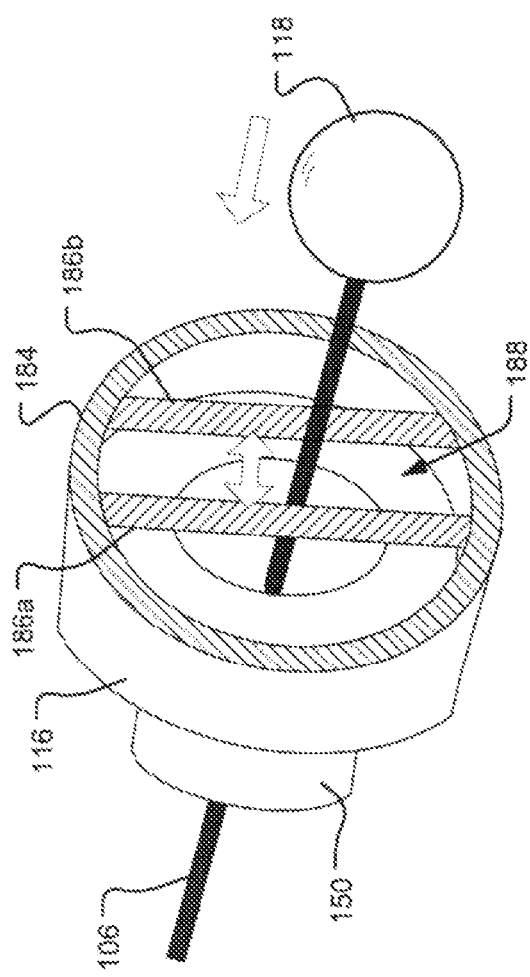
FIG. 10 is a schematic isometric view in partial cross section of a further embodiment of a retention structure in the form of a slot bounded by parallel wires or posts for retaining the distal end of the distal control wire within a distal engagement feature.

FIG. 10 depicts an additional exemplary implementation of an interface structure between the distal control wire 106 and the engagement feature 116 in the distal retaining feature 112. In this embodiment, a precision aperture for the access channel 150 is again not required and the diameter of the access channel 150 may be oversized to allow clearance around the lock ball 118. To provide the desired force control for release of the distal control wire 106 from the distal retaining feature 112, a pair of parallel bars 186a/b may be used. The bars 186a/b may be positioned within the engagement feature 116 and on opposing sides of the distal control wire 106. In one exemplary embodiment, the parallel bars 186a/b may be formed of two short sections of wire embedded in a sidewall 184 of the engagement feature 116, in the exemplary embodiment shown in FIG. 10 appearing as chords of the circular cross section of the cylindrical sidewall 184 of the engagement feature 116. In another exemplary embodiment, the parallel bars 186a/b may be formed as two integrally molded bars extending as chords of the circular cross section of the cylindrical sidewall 184. It may be appreciated that in other embodiments, more than two bars could be provided, e.g., three forming a triangle, four forming a square, etc. The width of the gap 188 between the bars 186a/b is smaller than the diameter of the lock ball 118 on the control wire 106 so that the distal lock ball 118 is retained within the engagement feature 116. The width of the gap 188, the thickness of the bars 186a/b, the number of bars 186a/b, and the material properties (e.g., tensile and shear strength) of the metal, plastic, or other material used to form the bars 188a/b may be chosen to provide for the bars 186a/b to bend apart and widen the gap 188 under a specific force to allow the lock ball 118 to pass between the bars 188a/b for release of the distal control wire 106 from the distal retaining feature 112.

In designing structures for retention of the lock ball 118 in the engagement feature 116, several performance factors may be taken into consideration. One factor may be the force the particular retention mechanism withstands when holding the distal (or proximal) retainer when under load. In exemplary device designs for use with the devices disclosed herein, holding forces may be between 0.25 and 3 lbs. This range of force assures that the engagement feature 116 does not prematurely release the distal control wire 106 during deployment of the occlusion device. An additional factor to consider is the force required to retract the distal lock ball 118 from the engagement feature 116. In exemplary implementations, this force may range from 0.25 to 5 lbs, depending on the absolute and relative dimensions of the components. Maintaining a narrow range and repeatable force for disposable devices such as those disclosed herein is challenging and requires highly precise dimensions, which are not always cost effective. Thus, the implementations shown in FIGS. 7A-10 and other similar concepts allow the introduction of some additional dimensional flexibility in the design in order to reduce the precision required yet still produce a relatively narrow range of forces for release. For designs in which the retention and release force work in the same axis, the force to release may be somewhat higher than the retention force performance and that margin of difference between these forces should be repeatable as well.

Figure 11:
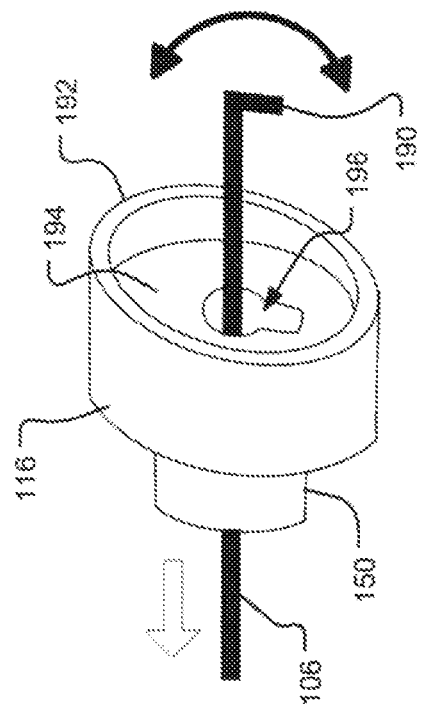
FIG. 11 is a schematic isometric view of another embodiment of a retention structure based upon rotational position in the form of a keyhole for retaining the distal end of the distal control wire having a key feature within a distal engagement feature.

FIG. 11 depicts an additional exemplary implementation of an interface structure between the distal control wire 106 and the engagement feature 116 in the distal retaining feature 112. In this embodiment, no precision aperture for the access channel 150 is required. In this implementation, the distal end of the distal control wire is formed as a key 190 and the lumen of the access channel 150 is formed as a keyway 196. Notably, the key hole design eliminates the release force issue discussed above. Instead of requiring a force to release the distal control wire 106 from the engagement feature 116, this approach uses a different mechanism. During placement of the occlusion device, the distal control wire 106 is oriented by the physician such that the key 190 on the distal end of the distal control wire 106 interfaces with or engages a shelf 194 or other surface defining the keyway 196 between the sidewalls 192 of the engagement feature 116. In order to remove the distal control wire 106 from the distal retaining feature 112, the physician must rotate the distal control wire 106 such that the key 190 aligns with the complementary keyway opening 196 in the engagement feature 116. When the key 190 and the keyway 196 are aligned, the key 190 passes through the keyway 196 in the access channel 150 allowing the distal control wire 106 to be released from the engagement feature in the distal retaining feature 112.

Figure 12B:
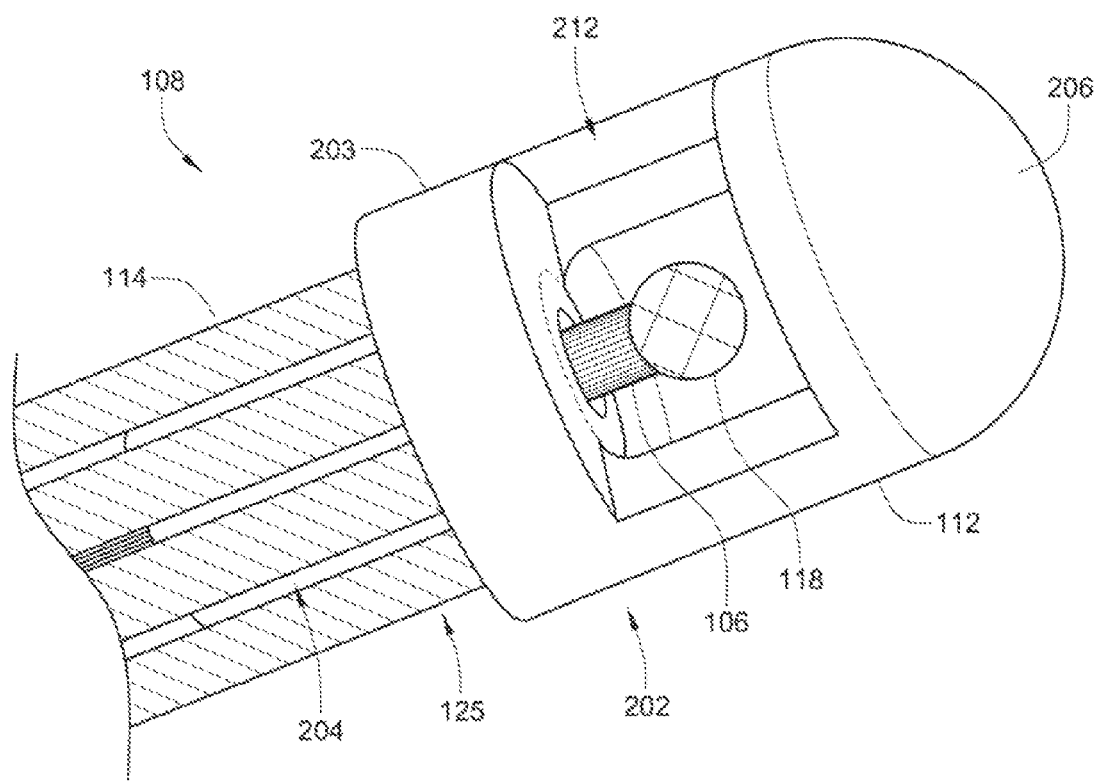

FIGS. 12A-B depict an additional exemplary embodiment of a distal retaining feature 112 of the occlusion device 108. In this embodiment, the distal retaining feature 112 is configured as a hub having a head portion 202 and proximally located stem portion 204. The stem portion 204 has a relatively smaller latitudinal dimension (or width) than the head portion 202 to accommodate attachment of the coil members 114 as shown in FIG. 12B. In this embodiment, the proximal end 203 of the head portion 202 steps immediately outward from the narrower stem portion 204, although a sloping or gradual transition can be used. The distal ends 125 of the coil members 114 can be coupled directly to the stem sidewall 205 such that the distal terminus of each coil member 114 is adjacent (or abutting) the proximal end 203 of the head portion 202. Techniques for attachment include the use of, e.g., adhesive, thermal bonding, a crimp, wrap, tie, or band, and other methods available to those of ordinary skill in the art.

Both the head portion 202 and the stem portion 204 preferably have cylindrical (or substantially cylindrical) bodies, with the head portion 202 having an atraumatic dome 206. Other shapes can be used for the head portion 202 and the stem portion 204, such as ones having elliptical, polygonal, and/or asymmetrical cross sections, to name a few. The atraumatic dome 206 is hemispherical in shape, but other atraumatic configurations can be used as well.

As shown in FIG. 12A, a sidewall 208 extends partially around the perimeter of the head portion 202 such that a gap (or opening) 210 is present. Both a retention chamber 153 (for housing the stopper element 118) and the access channel 150 (that permits passage of the distal control wire 106) can be seen through this gap 210.

In one embodiment, the gap 210 can be used to facilitate the assembly process by permitting insertion of the stopper element 118 (having a larger lateral dimension than the access channel 150) through the gap 210 and into the retention chamber 153, where the stopper element 118 can then be coupled with the distal control wire 106 to form the arrangement depicted in FIG. 12B. A sidewall insert 212 (shown in FIG. 12B) can then be placed into the gap 210 and fixed to the head portion 202 (e.g., by adhesive or thermal bonding) in order to fully house, or encapsulate, the stopper element 118 within the retention chamber 153. This can protect against the entry of bodily fluids or other objects that may inhibit proper release of the distal retention feature 112.

In another embodiment, the gap 110 can permit the insertion, into the retention chamber 153, of any of the elements (e.g., 170, 172, 180, 184, 194) for resisting passage of the distal control wire 106 that are described with respect to FIGS. 7A-11. In these embodiments, the stopper element 118 will preferably have a lateral dimension that is less than that of the access channel 150, although it can be greater as well.

The sidewall insert 212 preferably has an outer surface that is shaped to match, or conform to, the outer surface of the head portion 202. The sidewall insert 212 can also be radiopaque, or have enhanced radiopacity as compared to the rest of head portion 202, which could be advantageous when the head portion 202 is fabricated from a polymer lacking pronounced radiopacity (e.g., PEEK). The sidewall insert 212 can be made radiopaque in a number of ways, such as by fabricating the insert 212 out of a radiopaque material (e.g., platinum, gold, tantalum, and alloys based on these materials) or by fabricating insert 212 out of the same material as the head portion 202 and then coupling a radiopaque material thereto. Of course, any other part of the distal retaining feature 112 can be made radiopaque if so desired.

Figure 13A:
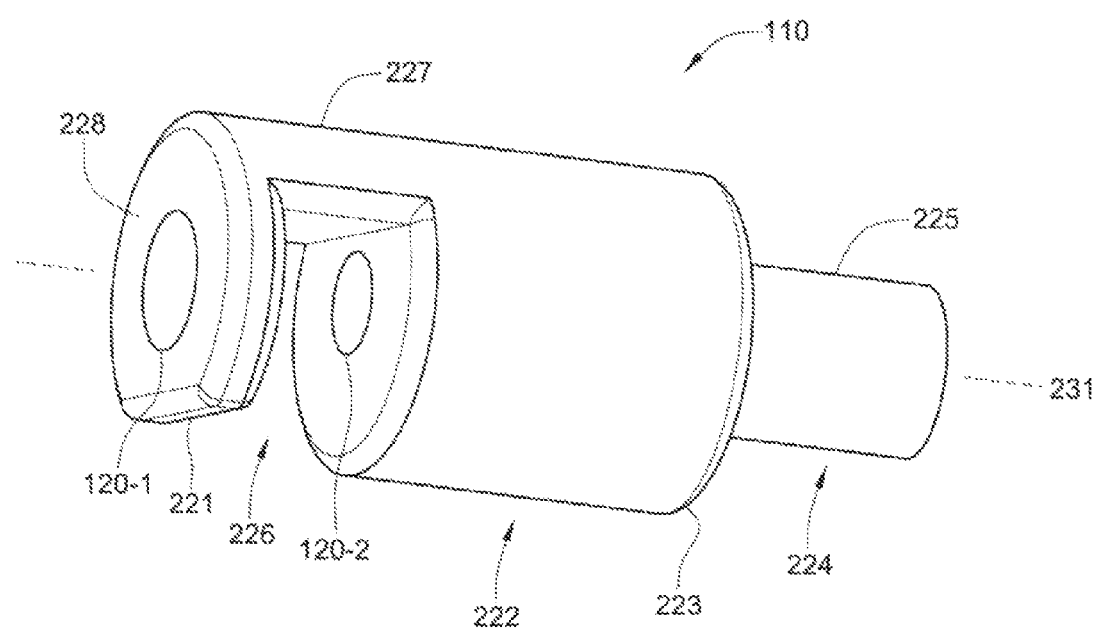
FIG. 13A is a perspective view of an exemplary embodiment of a proximal retaining feature.
Figure 13B:
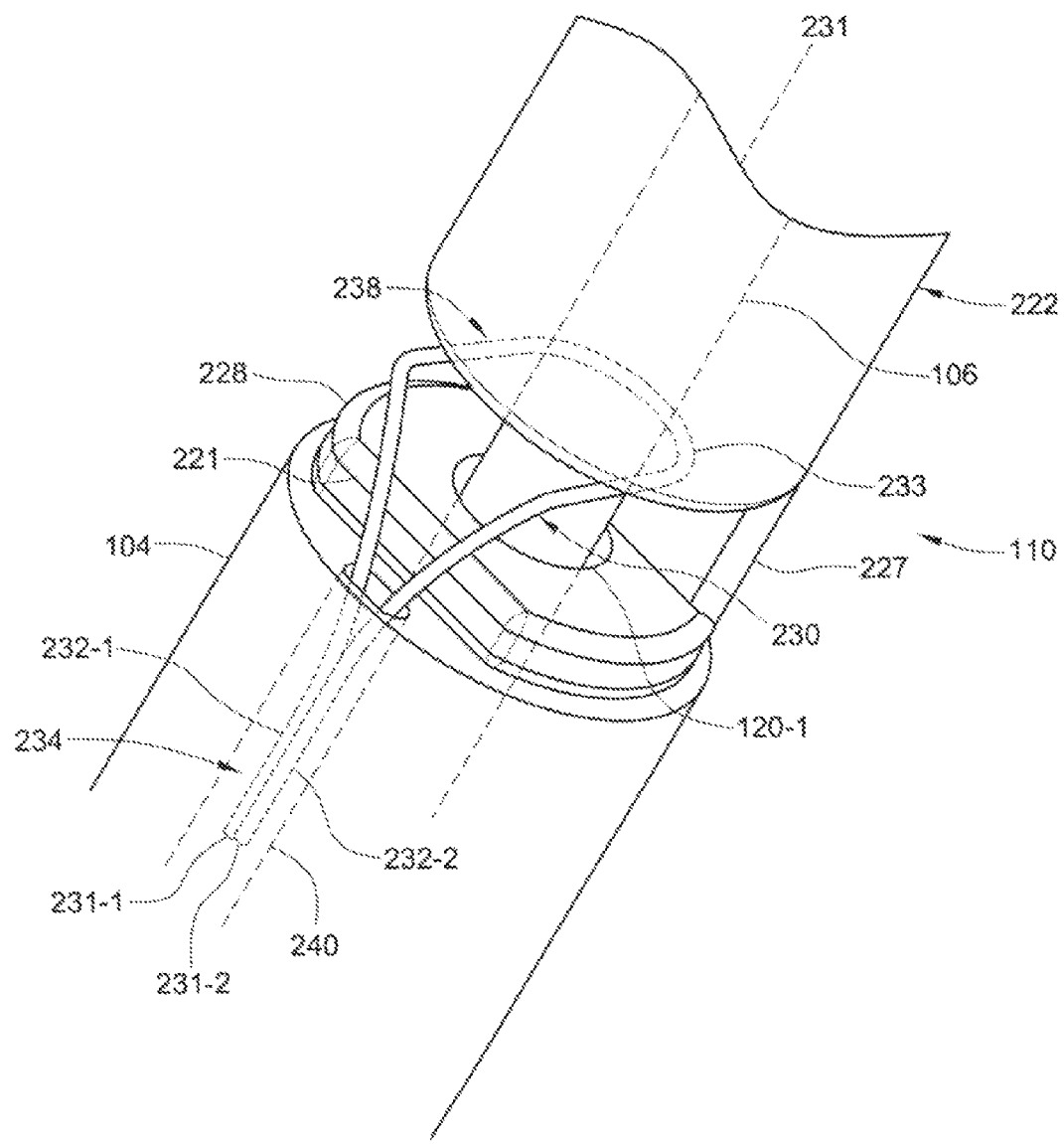
FIG. 13B is a perspective and partial cross-sectional view of the exemplary embodiment of the proximal retaining feature of FIG. 13A used in conjunction with an exemplary embodiment of the occlusion apparatus.

Turning now to the opposite end of the implant, FIGS. 13A-B depict another exemplary embodiment of the proximal retaining feature 110. Here, similar to the previous embodiment, the proximal retaining feature 110 is configured as a hub having both a head portion 222 and, in this case, a distally located stem portion 224, which has a relatively smaller latitudinal dimension (or width) than the head portion 222 to accommodate attachment of the proximal ends 123 of the coil members 114 (not shown). In this embodiment, the distal end 223 of the head portion 222 steps immediately outward from the narrower stem portion 224, although a sloping or gradual transition can be used. The proximal ends 123 of the coil members 114 (again, not shown) can be coupled directly to the stem sidewall 225 such that the proximal terminus of each coil member 114 is adjacent (or abutting) the base 223. The same techniques for attachment can be used as described in the previous embodiment.

Both the head portion 222 and the stem portion 224 preferably have cylindrical (or substantially cylindrical) bodies, with the head portion 222 having one or more lateral (side) windows 226. Other shapes can be used for the head portion 222 and the stem portion 224, such as ones having elliptical, polygonal, and/or asymmetric cross sections, to name a few.

Here, the head portion 222 has a single window (or opening) 226 opposite the proximally extending sidewall (or strut)

227. The window 226 can be alternatively described as a gap in the sidewall of the proximal retaining feature 110. The proximal end 228 of the head portion 222 is in the form of a lip or plate-like cover. An access channel 120-1 extends through the proximal end 228 and continues, as access channel 120-2, through the main body of the head portion 222 so as to accommodate passage of the distal control wire 106 therethrough. The periphery (or edge) of the head portion proximal end 223 has an end-on profile that is generally circular with one side truncated such that it has a generally straight edge 230 akin to a chord of a circle. This edge 230 is located radially closer to the longitudinal axis 231 of the proximal retaining feature 110 than is the side surface of the more distally located main body of the head portion 222, and accommodates passage of an engagement element over the edge 230 and into the side window 226.

An example embodiment of such an engagement element is depicted in FIG. 13B. Here, the engagement element 230 engages with the distal control wire 106 and prevents the proximal end of the occlusion device 108 from moving with respect to the distal end of the pusher 204. Retraction of the distal terminus of the control wire 106 proximally past the engagement element 230 disengages the element 230 and permits complete release of the occlusion device 108.

The engagement element 230 can be configured as (or with) a loop that can reliably maintain engagement with the distal control wire 106, for instance, with one side of the loop passing or extending around the control wire 106 so as to substantially or completely surround the control wire 106. The system can be configured such that the loop encircles only the control wire 106. The engagement element 230 can act as a tether and can be formed from wire, ribbon, a filament, or suture and can be composed of nitinol, stainless steel, polymers, and the like.

In FIG. 13B, the engagement element 230 is a flexible loop formed from a single wire body doubled back upon itself. The wire loop is preferably fabricated from nitinol and heat treated so as to retain its shape (i.e., preset or preformed). In the shape depicted here, both termini 231-1 and 231-2 of the wire body are proximally located within a lumen 240 of the pusher 104, and the legs 232-1 and 232-2 of the wire body extend in a substantially longitudinal direction over the proximal end 228 of the head portion 222. At that location, the legs 232-1 and 232-2 bend into an orientation transverse to the longitudinal axis 231 such that they extend in a substantially latitudinal direction and come together to form loop 233 around the distal control wire 106 (between access channels 120-1 and 120-2). It should be noted that one or more legs can be used.

A proximal portion 234 of the wire body is preferably securely coupled (i.e., fixed or anchored) within the lumen 240 such that the wire body, as a whole, cannot slide in relation to the pusher 104. In the embodiment of FIGS. 13A-B, the proximal portion 234 includes the legs 232-1 and 232-2. The proximal portion 234 can be fixed within the lumen 240 using, e.g., mechanical means or adhesive. Alternatively, the proximal portion 234 can be embedded or encapsulated in the pusher sidewall during a fusion process. The proximal portion 234 can also be coupled directly to the outer surface of the pusher sidewall, such as with adhesive or a mechanical band, tie, or crimp, which can also be radiopaque (see the embodiment described with respect to FIG. 17). Preferably, the proximal portion 234 does not extend along the entire length of the pusher 104 so as not to, for example, reduce the flexibility of the pusher 104 or hinder the ability of the catheter to navigate tortuous vasculature.

A distal portion 238 of the engagement element 230 is flexible so as to bend between the transverse orientation shown in FIG. 13B and a substantially longitudinal orientation shown in FIG. 13C. After the terminus of the distal control wire 106 is retracted past the engagement element 230, the occlusion device 108 is no longer attached to the pusher 104. Proximal retraction of the pusher 104 pulls the distal portion 238 of the engagement element 230 against the proximal end 228 of the occlusion device 108 and causes the distal portion 238 to deflect from the transverse orientation to the substantially longitudinal orientation (e.g., by approximately 90 degrees).

This distal portion 238 of the engagement element 230 (including the bend) is preferably substantially flexible such that it deflects readily upon retraction of the pusher 104. This keeps the looped wire body from catching or hanging up on the proximal end 230 of the occlusion device 108, thereby preventing the application of a torque (or angular momentum) to the occlusion device 108 or dislodging the proximal end 228 of the occlusion device 108 from the primary coil pack.

In order to assist deflection of the distal portion 238 and provide a low friction release mechanism, the proximal retaining feature 110 can be configured with a sloped surface (e.g., slide or ramp), that allows the distal portion 238 to more easily transition out of the window region 226. FIG. 13D depicts an exemplary embodiment having a slide 239. Here, the slide 239 has a constant angle of about 45 degrees. Steeper or shallower angles can be used, as can angles that vary along the length of the proximal retaining feature 110. The slide 239 is oriented such that the proximal end portion 228 of the proximal retaining feature 110 is thicker (in the longitudinal direction) on the side that is adjacent strut 227 and thinner on the side that is adjacent the window 226. In addition to providing the slide 239, or as an alternative, the engagement element 230 can be biased such that the distal portion 238 automatically transitions towards the substantially longitudinal orientation as the implant is released from the pusher.

Figure 14A:
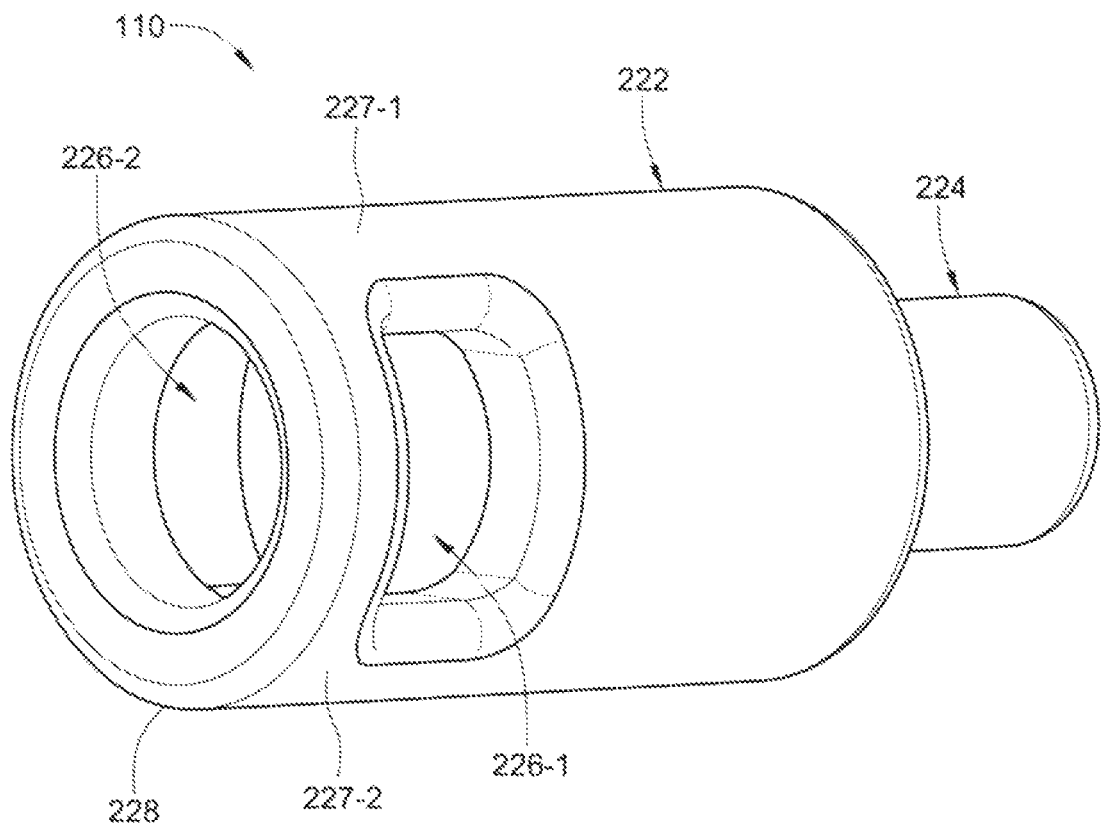
FIG. 14A is a perspective view of another exemplary embodiment of a proximal retaining feature.
Figure 14B:
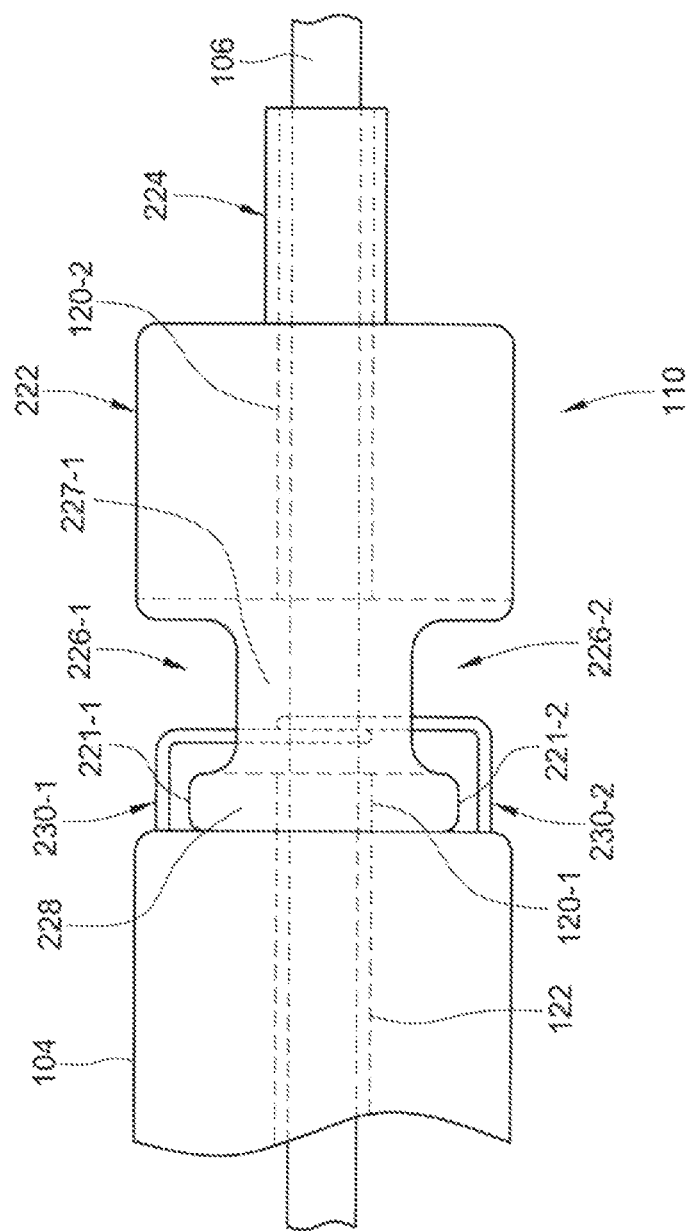
FIG. 14B is a side and partial cross-sectional view of another embodiment of the proximal retaining feature of FIG. 14A used in conjunction with another exemplary embodiment of the occlusion apparatus.

The proximal retaining feature 110 can also be configured with more than one window 226 to accommodate multiple engagement elements 230. FIGS. 14A-B depict an exemplary embodiment of the proximal retaining feature 110 having two side windows 226-1 and 226-2 separated by struts 227-1 and 227-2. The side windows 226-1 and 226-2 are preferably located symmetrically, i.e., laterally opposing each other at the same position along the longitudinal axis of the retaining feature 110, to allow for uniformity during the release procedure. Likewise, as shown in FIG. 14B, the engagement elements 230-1 and 230-2 would preferably be positioned in symmetrical locations on the pusher 104 and would each extend into a different window 226-1 and 226-2, respectively. From there the elements 230-1 and 230-2 extend over the distal control wire 106 from opposite directions, with one element 230-1 lying directly beneath the other element 230-2. A configuration where the elements 230 are not lying next to each other but are gapped apart is also possible, although that is a less symmetrical arrangement.

In the case of three engagement elements 230, the center of each window 226 would preferably be located 120 degrees apart with the engagement elements 230 coupled to the pusher 104 in locations corresponding to those of the windows 226. In any of these multi-window embodiments, and as shown in FIG. 14B, the proximal end 228 of the retaining feature 110 can have a truncated edge 230 located proximal to each window 226 to allow for passage of the engagement element 230 without increasing the overall device profile.

Figure 15:
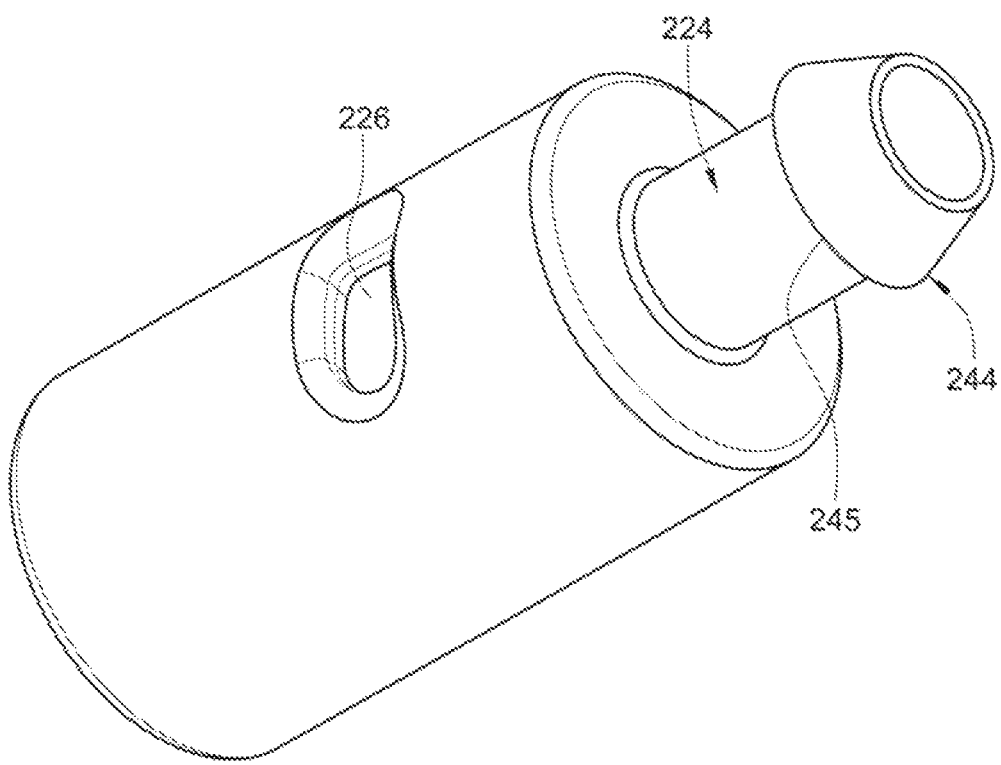
FIG. 15 is a perspective view of another exemplary embodiment of a proximal retaining feature.

FIG. 15 depicts another exemplary embodiment of the proximal retaining feature 110. Here, the stem portion 224 includes a flared (or barbed) end 244 with a pronounced ridge 245. The ridge resembles a serration and increases the surface friction between the coil members 114 (not shown) and the stem portion 224 itself, to reduce the likelihood that the coil members will detach. Multiple such flares can be used along the length of the stem portion 224. Also, other features that enhance the surface friction can be used such as a textured or abrasive surface, multiple grooves (or recessions), and the like.

It should also be noted that in this and the other embodiments described herein, the stem portion (e.g., 204, 224) can be omitted altogether. This can be particularly useful with an implant having only a single coil, in which case the single coil is attached directly to the head portion (or main body) of the hubs.

The embodiments of the proximal retaining feature 110, especially those described with respect to FIGS. 12A-15, are suitable for use as a proximal release system for other types of medical implants and delivery systems as well. FIGS. 16A-D depict an exemplary embodiment of a stent 300 (suitable for use as a coronary or neuro-stent (e.g., for ischemia or neck-bridging), with or without a graft, etc.). Stent 300 is shown in a radially expanded state in FIG. 16A and in a radially compressed state in FIG. 16B. Stent 300 includes multiple interconnecting elastic struts 301 with expandable open cells 302 formed therebetween. Where struts 301 intersect at the proximal end 305 of the stent are four independently movable crowns 303-1 through 303-4. Proximal to each crown 303-1 through 303-4 is a lobe (or extension) 304-1 through 304-4, respectively. Each of the lobes 304 has an eyelet therein. Two of the lobes, 304-1 and 304-3, each have radiopaque (e.g., Pt) markers 307-1 and 307-3 fixed within the eyelets and the other two lobes, 304-2 and 304-4, have open eyelets, 306-2 and 306-4, through which an engagement element can pass. It should be noted that usage of the terms "crown" and "lobe" herein are not intended to be mutually exclusive in all contexts.

Four independently movable crowns 303-5 through 303-8 are also present on the distal end 314. A radiopaque marker 309-1 through 309-4 is crimped, bonded, welded, or otherwise coupled to each of the distal crowns 303-5 through 303-8, respectively. In this embodiment, each marker 309-1 through 309-4 is in the form of a sleeve placed over top the (preferably) elongate strut-like crowns 303-5 through 303-8. Each sleeve 309-1 through 309-4 can have either an open or a closed distal terminus. Although the stent in FIG. 16A has a different type of radiopaque marker at each end, the different types can be used on either end and mixed as desired.

The overall device 300 is preferably constructed by cutting, etching, or otherwise forming the struts, cells, crowns, and eyelets in a hypotube fabricated from nitinol, other nickel titanium alloys, stainless steel, or the like. This can be done with a hypotube having a diameter corresponding to the stent in either the compressed state, the expanded state, or an intermediate state between the two. The various radiopaque markers are then coupled (e.g., adhesively bonded, welded, crimped, wrapped, tied, or otherwise secured) to the device body, followed by a heat treatment of the device so that it is biased towards its expanded state, which requires first expanding the hypotube if it is initially formed in a compressed or intermediate state.

Figure 16C:
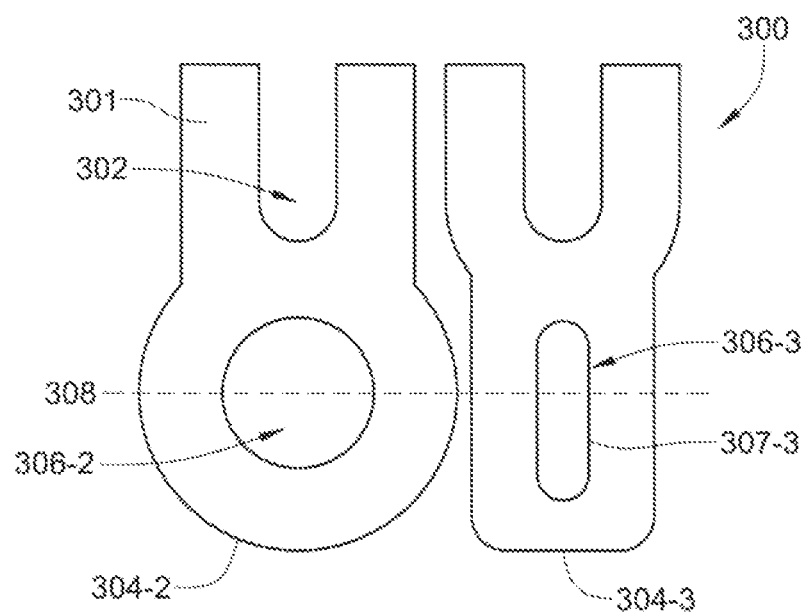
FIG. 16C is a side-by-side comparison of exemplary lobes from the embodiment of the stent of FIG. 16A.

FIG. 16C shows two lobes 304-2 and 304-3 in a side-by-side comparison as if the stent 300 was unrolled into a planar state. Lobe 304-2 with the open eyelet 306-2 has a relatively greater lateral dimension along the common axis 308 than lobe 304-3. This configuration allows a sufficiently large opening 306-2 through which the engagement element can pass, while at the same time allowing for the presence of a radiopaque marker 307-3 within the narrower space of the adjacent eyelet 306-3.

Figure 16D:
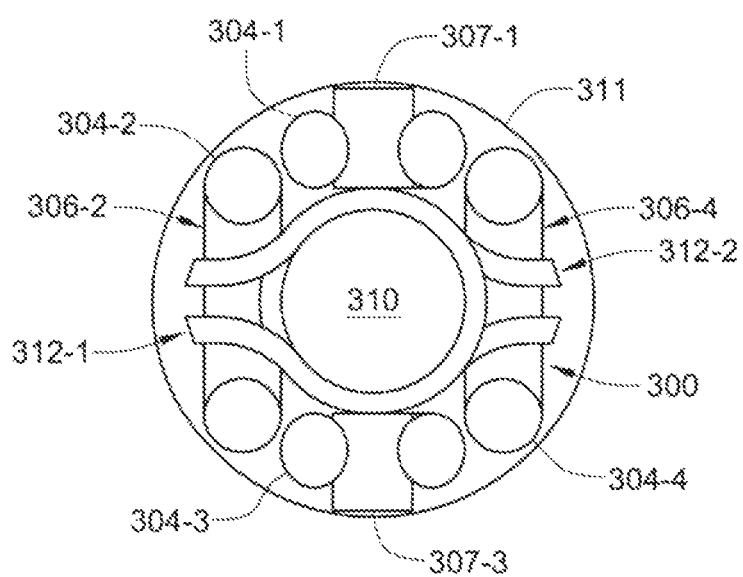
FIG. 16D is an end-on view of an exemplary embodiment of a stent delivery system.

The four crown stent 300 can then be reduced to a highly compressed radial state as shown in the cross-sectional view of FIG. 16D. Here, the inner wall 311 of the delivery catheter is shown surrounding and preferably maintaining the stent 300 in the compressed state. A control wire 310 is slidably received within the inner lumen of the stent 300 and two engagement elements 312-1 and 312-2 are looped around the control wire 310 through the open eyelets 306-2 and 306-4. A pusher (not shown) has an inner lumen that slidably receives the control wire 310. The pusher would be fixed to the proximal ends of the engagement elements 312-1 and 312-2 in one of the manners described above.

After deployment of the stent 300 from within the catheter, the control wire 310 can be proximally retracted to release the engagement elements 312-1 and 312-2, at which point the proximal end of the stent 300 can self-expand, pulling the loop elements 312-1 and 312-2 back through the eyelets 306-2 and 306-4, and freeing the stent 300 from the pusher. While this embodiment has been described with respect to a four crown stent 300, the alternating open eyelet and marker-bearing eyelet technique can be repeated in a stent with greater than four crowns to offer a stent release system with increased compactability. It should be noted that the stent 300 can be used with any embodiment of a proximal retaining feature described herein.

The proximal retaining features described herein can also be used with vena cava filters, aneurysm neck bridges, and embolic cages such as those described in U.S. Pat. No. 5,916, 235 ("Apparatus and Method for the Use of Detachable Coils in Vascular Aneurysms and Body Cavities" naming Guglielmi), which is fully incorporated by reference herein for all purposes.

FIG. 17 is a side view depicting an exemplary embodiment of an embolic cage 400 having a distal hub 402 (housing a radiopaque marker) and a proximal hub 404. The device 400 is preferably constructed by cutting, etching, or otherwise forming the device from, a hypotube. In this example, the hubs 402 and 404 remain in their tubular form and the remainder of the device has been expanded outward. The device can be constructed in a manner similar to that described with respect to FIGS. 16A-B.

On the proximal side, two of the crowns 403-2 (obscured) and 403-4 are joined together at the proximal hub 404 and the remaining crowns 403-1 and 403-3 remain free. Similarly, on the distal side, two of the crowns 403-6 (obscured) and 403-8 are joined together at the distal hub 402 and the remaining crowns 403-5 and 403-7 remain free. (Having all of the proximal crowns connected to the proximal hub 404 would allow retrievability of the device 400 into the catheter, thereby enabling usage as a stentriever, in which case any number of one or more distal crowns 403 can couple to the distal hub 402.)

In the embolic cage embodiment depicted here, the proximal hub 404 is open and allows for the passage of a control wire 405 therethrough. A pusher (or delivery catheter) 406 slidably receives the control wire 405 through an inner lumen. The pusher 406 is in contact with the terminus of the proximal hub 404 and an engagement element 408 is connected to the outer surface of the pusher 406 and held in place by an overlaid band 410, which can be radiopaque. The engagement element 408 is sized small enough to extend distally just past the proximal hub 404 when the pusher 406 is in close contact. The control wire 405, when extended moderately past the proximal hub 404, will then hold the engagement element 408 taught and thereby couple the pusher 406 to the embolic cage 400. At the desired time of release, the control wire 405 can be proximally retracted through the proximal hub 404 to free the looped engagement element 408. It should be noted that the embolic cage 400 can be used with any embodiment of a proximal retaining feature described herein.

It should also be noted that the embodiments described with respect to FIGS. 16A-17 can be used with coil-based occlusive implants having only one coil member or more than one coil member, and each coil member can be composed of a metal or a polymer.

The embodiments of the proximal retaining feature 110 described with respect to FIGS. 12A-17 exhibit superior attributes over the prior art. This is particularly true in the context of treating cerebral aneurysms and occluding vasculature. For instance, in these embodiments the engagement element is secured directly to the pusher and made releasable from the implant. This ensures that the engagement element is not left behind in the patient's body. Reversing the engagement element such that it is secured to the implant and made releasable from the pusher would require leaving the engagement element behind, where it is essentially free to hang or dangle within the bloodstream, which can result in undesirable thrombus formation. For example, for an implant deployed within an aneurysm, the engagement element could extend through the aneurysm neck and into the parent vessel, where blood flow should remain unimpeded. Because the engagement element is in a hanging state, it is free to move and contact adjacent bodies or swing within the blood stream, thereby increasing the risk that a thrombus on the engagement element will become dislodged and embolize.

As another example, in the embodiments of FIGS. 12A-17 the engagement element is secured to the pusher in a distal end region of the pusher and is not configured as, nor does it couple with, a pullwire that extends the length of the catheter to an accessible position outside of the patient's body. Such a pullwire configuration raises the complexity of the device as both the engagement element and the control wire must extend the entire length of the catheter. This could require the outer diameter of the catheter to be increased to fit the engagement element, which is undesirable (and in some cases not possible) in many applications. It could also force other components to be reduced in size, which, in turn, decreases the stress tolerances of those components, making the possibility of failure more likely. As already mentioned, the presence of the engagement element along the length of the catheter reduces that catheter's flexibility and increases the difficulty in navigating tortuous vasculature. It also requires the physician to perform an additional step in the release of the implant, increasing the time necessary to complete the procedure as well as the complexity of the procedure itself. If a proximal handle or control device is used (as it can be for all embodiments described herein), then that handle requires an additional actuator to control the pullwire.

Another attribute is the manner of attachment of the engagement element to the pusher, e.g., either embedded within the pusher wall or secured to the outer surface of the pusher. In these locations, the engagement element does not interfere with the sliding movement of other components through the open distal end of the pusher and, more importantly, the friction created by the sliding movement of other components (such as a core wire) does not urge the engagement element in the same direction as that sliding component. For instance, were the engagement element to extend through the open distal end of the pusher, distal movement of a core wire would pull or tug on the engagement element and could cause it to break free of the pusher. Conversely, proximal movement of the core wire could cause the engagement element to tighten around the core wire, impeding movement of the core wire and release of the implant.

Yet another attribute of certain embodiments is that the engagement element passes through a window in the sidewall of the proximal hub (as opposed to, e.g., over a strut or pin attached across a proximal end opening of the implant). For instance, in the embodiments of FIGS. 14A-15, the window is directly in the curved sidewall of the hub, with a substantial portion of the sidewall located proximal to the window. The size of this sidewall portion and its curvature increase its resistance to buckling as the engagement element transitions into the substantially transverse orientation. In the embodiments of FIGS. 13A-B, the plate-like proximal end 228 of the hub is provided with ample support by the sidewall strut 227.

A further attribute is that the control wire is not woven through the implant, which avoids the risk that the control wire will become inadvertently bound or stuck with respect to the implant. In many of the embodiments herein, the control wire can extend directly into the implant, e.g., without passing through the implant in a woven or interlaced manner.

Another attribute of certain embodiments is that the central (or inner) lumen of the pusher need only accommodate the control wire. In other words, the central lumen of the pusher can be adapted to slidably receive only the control wire, or the central lumen of the pusher can be filled (or substantially filled) with the control wire. This allows a minimization of pusher diameter, which in turn allows further reduction in the overall catheter diameter.

And yet another attribute of certain embodiments is the fact that the control wire is freely slidable with respect to the pusher and requires no threaded (or other locking) interface, such as those that require rotation to move the core wire proximally. Such interfaces are difficult to implement as a rotation applied at the proximal end of the core wire tends to cause the core wire to twist along its length, instead of inducing a corresponding rotation at the location of the threads.

The preceding paragraphs discussing the "attributes" of various embodiments in relation to the prior art should not be interpreted as a disavowal of claim scope, nor should they be used to define a claimed invention beyond the explicit language of the claim itself.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Non-limiting inclusive terms (e.g., comprising, including, and having) are to be construed as being open-ended, while limiting inclusive terms (e.g., consisting of) are to be construed as closed-ended. Also, the term "end" is used generally herein to include the terminus as well as the region of the structure adjacent to the terminus. As such, the terms "end region" and "terminus" have antecedent support in the specification by virtue of the contents of the figures and the multiple usages of the term "end" herein. The terms "end region" and "terminus" can thus be used in the claims included herewith or presented at a later date. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A system for occluding a biological lumen, comprising:
an occlusive implant having a proximal hub and a distal hub that are movable towards each other;
an elongate pusher having an inner lumen;
an engagement element having a proximal portion and a distal portion, wherein the proximal portion is secured within a sidewall of the elongate pusher such that the engagement element is not wholly slidable with respect to the pusher and wherein the engagement element is a flexible wire or thread; and
a control wire slidably received within the inner lumen of the pusher,
wherein a distal end of the control wire is releasably coupled to the distal hub of the implant such that the distal hub of the implant is moveable with the control wire and releasable from the control wire,
wherein the proximal hub of the implant comprises a proximal end having a lumen through which the control wire can slide and a side window located distal to the proximal end of the proximal hub, and the distal portion of the engagement element is adapted to pass through the side window and engage with the control wire to maintain coupling of the proximal hub to the pusher,
wherein the engagement element is releasably coupled to the control wire such that no portion of the engagement element extends through an open distal end of the pusher through which the control wire extends, and
wherein the engagement element can be released from the control wire and the proximal hub upon retraction of the control wire from the proximal hub.

2. The system of claim 1, wherein the occlusive implant comprises a plurality of coil members each having a distal end coupled with the distal hub and a proximal end coupled with the proximal hub.

3. The system of claim 1, wherein the control wire has a longitudinal axis, and the distal end of the control wire has a width that is larger than a width of a shaft of the control wire, the distal hub of the implant being adapted to impede proximal motion of the distal end of the control wire with respect to the distal hub until the application of a threshold force.

4. The system of claim 3, wherein the distal end of the control wire is a stopper element.

5. The system of claim 4, wherein the distal hub of the implant comprises an access channel having a width that is less than the width of the stopper element, wherein at least one of the access channel and the stopper element are deformable upon the application of the threshold force.

6. The system of claim 4, wherein the distal hub of the implant comprises a ring element having an opening with a width that is less than the width of the stopper element, wherein the ring element is deformable upon the application of the threshold force.

7. The system of claim 6, wherein the ring element is a split ring.

8. The system of claim 4, wherein the distal hub of the implant comprises a ring element having a plurality of tabs extending into a central opening of the ring element, the plurality of tabs being deformable upon the application of the threshold force.

9. The system of claim 4, wherein the distal hub of the implant comprises one or more bars that are bendable upon the application of the threshold force.

10. The system of claim 4, wherein the distal hub has an atraumatic dome and a sidewall opening covered by a radiopaque insert.

11. The system of claim 1, further comprising a coupling wire having a first end coupled to a lock element and a second end coupled to the pusher, and wherein the proximal hub of the implant includes an inner lumen with a chamber for housing the lock element.

12. The system of claim 11, wherein the lock element is held within the chamber by the presence of the control wire adjacent to the chamber, and wherein the lock element is releasable from the proximal hub upon removal of the control wire from the proximal hub.

13. The system of claim 11, further comprising an elongate lock wire slidably received within the inner lumen of the pusher, wherein the lock element is held within the chamber by the presence of the control wire and the lock wire adjacent to the chamber, and wherein the lock element is releasable from the proximal hub upon removal of the control wire and the lock wire from the proximal hub.

14. The system of claim 1, wherein the pusher has a longitudinal axis along its length, and wherein the engagement element comprises a leg coupled with a looped portion, the engagement element being preset such that the at least one leg extends substantially longitudinally from a proximal terminus to the looped portion, which is in a substantially transverse orientation with respect to the longitudinal axis.

15. The system of claim 1, wherein the proximal hub comprises a sloped surface.

16. The system of claim 1, wherein the side window is a first side window and the engagement element is a first engagement element, the proximal hub further comprising a second side window located distal to the proximal end of the proximal hub, the system further comprising:
a second flexible engagement element having a proximal portion secured to the pusher and a distal portion adapted to pass through the second side window and couple to the control wire to maintain coupling of the proximal hub to the pusher.

17. The system of claim 1, wherein the occlusive implant comprises one or more coil members.

18. The system of claim 17, wherein the one or more coil members are metal.

19. The system of claim 17, wherein the one or more coil members are polymeric.

20. The system of claim 1, wherein the control wire has a longitudinal axis, and the distal end of the control wire has a width that is larger than a width of a shaft of the control wire, the distal hub of the implant being adapted to impede proximal and distal motion of the distal end of the control wire with respect to the distal hub.

21. The system of claim 1, wherein the engagement element is a nitinol wire.

\* \* \* \* \*